United States Patent [19]

Ichijima

[11] Patent Number: 4,737,451

[45] Date of Patent: Apr. 12, 1988

[54] SILVER HALIDE COLOR PHOTOGRAPHIC MATERIAL

[75] Inventor: Seiji Ichijima, Kanagawa, Japan

[73] Assignee: Fuji Photo Film Co., Ltd., Kanagawa, Japan

[21] Appl. No.: 916,428

[22] Filed: Oct. 7, 1986

[30] Foreign Application Priority Data

Oct. 7, 1985 [JP] Japan ................. 60-223343

[51] Int. Cl.$^4$ ................................ G03C 7/32
[52] U.S. Cl. ............................ 430/544; 430/223; 430/553; 430/555; 430/557; 430/558; 430/955; 430/957; 430/959
[58] Field of Search ............... 430/223, 955, 957, 959, 430/553, 555, 557, 558, 382, 544

[56] References Cited

U.S. PATENT DOCUMENTS 4,248,962  2/1981  Lau .................................. 430/382
4,409,323  10/1983  Sato ................................. 430/544

Primary Examiner—Paul R. Michl
Assistant Examiner—Patrick A. Doody
Attorney, Agent, or Firm—Sughrue, Mion, Zinn, Macpeak & Seas

[57] ABSTRACT

A silver halide color photographic material comprising a support having thereon at least one silver halide emulsion layer, said color photographic material containing a compound capable of releasing a group upon reaction with an oxidation product of a developing agent, the resulting group is oxidized and undergoes a ring cleavage reaction whereby a photograhically useful group is cleaved.

The compound used in the present invention is capable of releasing a photograhically useful group through at least a two-step reaction, and the amount of the photographically useful group released is controlled depending on a concentration of the oxidation product of a developing agent. The silver halide color photographic material containing the compound either provides a color image having good image qualities such as sharpness, graininess, and color reproducibility, etc., or exhibits high sensitivity.

33 Claims, No Drawings

SILVER HALIDE COLOR PHOTOGRAPHIC MATERIAL

FIELD OF THE INVENTION

The present invention relates to a color photographic light-sensitive material containing a novel compound which is capable of rendering a photographically useful group utilizable during development processing.

BACKGROUND OF THE INVENTION

With color photographic light-sensitive materials based on the subtractive color process, various investigations have been made for the purpose of improvement in sharpness, improvement in graininess, improvement in color reproducibility, or increase of sensitivity.

Couplers which release a photographically useful group are one technique for accomplishing such purposes. Recently, in addition to couplers which release a photographically useful group from the coupling position thereof, couplers which release a photographically useful group through a timing group have been disclosed. Such couplers are disclosed, for example, in U.S. Pat. Nos. 4,248,962 and 4,409,323, etc. Further, another attempt wherein couplers which release a coupler capable of releasing a photographically useful group are utilized has been made as described in U.S. Pat. No. 4,438,193, etc.

In Japanese Patent Application (OPI) No. 138636/82 (the term "OPI" as used herein means an "unexamined published patent application"), there are disclosed examples of couplers capable of releasing an ED (electron donating) compound (a reducing agent). More specifically, the couplers described in Japanese Patent Application (OPI) No. 138636/82 can be represented by the formula

COUP—ED wherein COUP represents a photographic coupler residue capable of forming a dye image upon a reaction with the oxidation product of a color developing agent; and ED represents a group which is bonded to COUP at the coupling position of COUP and which is cleaved from COUP and is capable of undergoing an oxidation reduction reaction with the oxidation product of a color developing agent.

These compounds are, however, completely different from the compounds according to the present invention, since they are used only for the purpose of reducing the oxidation product of a developing agent. On the contrary, it is necessary that the compounds according to the present invention release a photographically useful group.

Although these known couplers exhibit improvement to some extent, it is not totally satisfactory, and further improvement has been desired.

SUMMARY OF THE INVENTION

Therefore, an object of the present invention is to provide a color photographic light-sensitive material which either provides a color image excellent in sharpness, graininess, and color reproducibility, and which has high sensitivity.

Other objects of the present invention will become apparent from the following detailed description and examples.

These objects of the present invention have been accomplished by a silver halide color photographic material comprising a support having thereon at least one silver halide emulsion layer, said color photographic material containing a compound capable of releasing a group, upon reaction with an oxidation product of a developing agent, which is oxidized and undergoes a ring cleavage reaction whereby a photographically useful group is cleaved.

DETAILED DESCRIPTION OF THE INVENTION

The compound which is used in the present invention is preferably represented by formula (I)

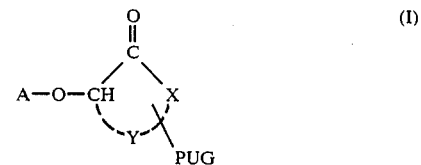

wherein A represents a coupler residue; X represents an oxygen atom, a sulfur atom or a substituted or unsubstituted imino group; Y represents an organic atomic group forming a 5-membered to 8-membered ring together with

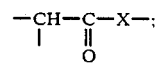

and PUG represents a photographically useful group or a precursor thereof.

The term "a coupler residue" as used herein means a monovalent group of coupler formed by removing a hydrogen atom from the coupling position of the coupler.

In formula (I), the atomic group represented by Y has a function of controlling a rate of oxidation of a hydroxy group which is formed by the cleavage of the bond between A and the oxygen atom to a carbonyl group. After the hydroxy group is oxidized to a carbonyl group, the bond between the carbonyl group adjacent to the carbonyl group thus formed and X is easily cleaved upon hydrolysis, X thus cleaved forms an anion, and, as a result of electron transfer from the anion, PUG is cleaved.

In the hydrolysis reaction upon which X is cleaved, a nucleophilic species such as a hydroxylamine, a paraphenylenediamine, etc., present at the development may nucleophilically attack the carbonyl group. Further, a mucleophilic agent (for example, hydroxamic acid, hydrazine, etc.) having a strong nucleophilicity to a carbonyl group is added to a developing solution of incorporated into a light-sensitive material whereby the rate of cleavage of X is increased. Such a nucleophilic reaction to a carbonyl group proceeds slowly when a hydroxy group is present at the α-position of the carbonyl group. However, the reaction rate significantly increases when the hydroxy group is oxidized to a carbonyl group. This is because the electrophilicity of the carbonyl group adjacent to X increases and the carbonyl group is rendered apt to be attached.

The compound according to the present invention generates PUG through the reaction of at least two steps as described above. When PUG represents a precursor of a photographically useful group, the photographically useful group is generated through a further reaction of one step. The present invention is characterized by passing through such a series of reactions. In the step of oxidation reduction reaction wherein oxidized compounds (for example, oxidation products of developing agents) present at the development react with other reactants and the rate of reaction depends on a concentration of each reactant. Specifically, reactants are immediately oxidized in a region where the oxidation products of the developing agents generate in a large amount. In contrast therewith, in a region where the oxidation products of the developing agents generate in a small amount, the oxidation reaction become slow. The principle of second order reaction described above coupled with the subsequent steps of the reaction brings about the effects of the present invention.

The compound represented by formula (I) may take the form of a tautomer as shown below, and the present invention includes both of these tautomers.

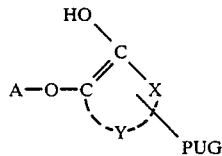

With the compound used in the present invention, the selection of A, X, Y and PUG is possible in a wide range and depending on the selection, the compound can be employed in various light-sensitive materials (for example, a color negative film, a color reversal film, a color positive film, etc.) according to various known methods. In general, the compound can be utilized as a DIR coupler, a colored coupler, a competing coupler, or a development accelerating coupler, etc., in mixture with a main coupler. In some cases it may be employed as a main coupler. The compound may be added to a high sensitivity layer, a low sensitivity layer, or a layer adjacent thereto, and a layer to be added is appropriately selected depending on the purpose. The term "main coupler" as used herein means a coupler which contributes most strongly to the color density of a coupling dye produced after development in the photographic layer containing said coupler.

As described above, the present invention includes a group of compounds which can be employed in various light-sensitive materials, by various methods to be used, and for various purposes. This is because the compound according to the present invention possesses several features, such as that the properties of a reaction product with the oxidation product of a developing agent can be varied (for example, variations of dyes formed, variations of colorless products) by an appropriate, selection of the coupling component represented by A; that the control of rate of release the group connected through the oxygen atom from A, control of rate of oxidation reaction of the hydroxy group to a carbonyl group, and control of rate of cleaving PUG can be easily varied by an appropriate selection of X and Y; and that the kind of photographic function can be varied depending on the particular purpose of an appropriate selection of PUG, etc.

The present invention is characterized in that the release of a photographically useful group is controlled depending on the concentration of the oxidation product of a developing agent and thus the area wherein PUG diffuses can be effectively controlled.

In formula (I), the coupler residue represented by A specifically include a yellow coupler residue (for example, an open-chain ketomethylene coupler, etc.), a magenta coupler residue (for example, a 5-pyrazolone coupler, a pyrazolotriazole coupler, a pyrazoloimidazole coupler, etc.), a cyan coupler residue (for example, a phenol coupler, a naphthol coupler, etc.), and a non-color forming coupler residue (for example, an indanone coupler, an acetophenone coupler, etc.), etc.

Yellow coupler residues include those as described in U.S. Pat. Nos. 3,265,506, 2,875,057 and 3,408,194, Japanese Patent Application (OPI) Nos. 29432/73, 66834/73, 13329/79 and 87650/75, etc.

Magenta coupler residues include those as described in U.S. Pat. Nos. 2,600,788, 3,062,653, 3,127,269, 3,419,391, 3,519,429 and 3,888,680, Japanese Patent Application (OPI) Nos. 111631/74, 171956/84 and 162548/84, etc.

Cyan coupler residues include those as described in U.S. Pat. Nos. 2,474,293, 2,801,171, 3,476,563, 4,009,035 and 4,333,999, Japanese Patent Application (OPI) Nos. 112038/75, 117422/75, 32071/80 and 109630/78, *Research Disclosure*, No. 15741, Japanese Patent Application (OPI) No. 204545/82, etc.

Coupler residues which substantially do not form a dye include those as described in U.S. Pat. Nos. 3,958,993 and 3,961,959, etc.

Further, the effects of the present invention are particularly exhibited when A in formula (I) represents a coupler residue represented by the formula (Cp-1), (Cp-2), (Cp-3), (Cp-4), (Cp-5), (Cp-6), (Cp-7), (Cp-8), (CP-9), (Cp-10), or (Cp-11) described below. These coupler residues are preferred because of their high coupling rates.

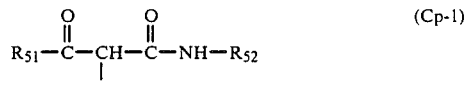

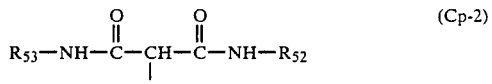

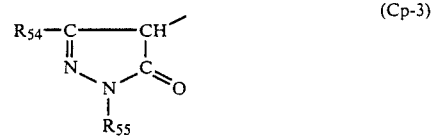

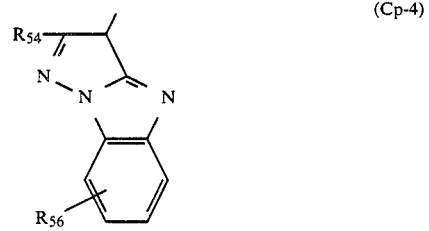

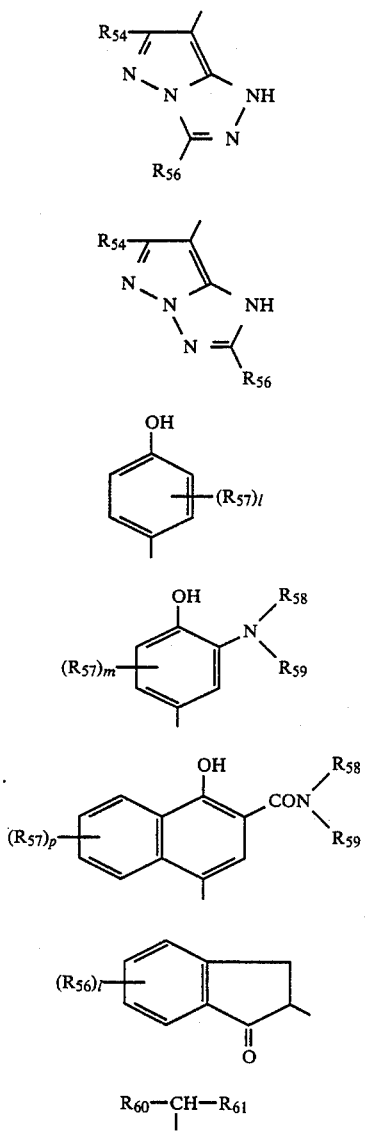

In the above-described formulae, a free bond attached to the coupling position indicates a position to which a group capable of being released upon coupling is connected. When $R_{51}$, $R_{52}$, $R_{53}$, $R_{54}$, $R_{55}$, $R_{56}$, $R_{57}$, $R_{58}$, $R_{59}$, $R_{60}$, or $R_{61}$ in the above-described formulae contains a diffusion-resistant group, it is selected so that the total number of carbon atoms included therein is from 8 to 32, and preferably from 10 to 22. On the other hand, when it does not contain a diffusion-resistant group, the total number of carbon atoms included therein is preferably not more than 15.

In the following, $R_{51}$ to $R_{61}$, l, m, and p in the above-described formulae (Cp-1) to (CP-11) are explained in further detail.

In the above-described formulae, $R_{51}$ represents an aliphatic group, an aromatic group, an alkoxy group or a heterocyclic group; and $R_{52}$ and $R_{53}$ each represents an aromatic group or a heterocyclic group.

The aliphatic group represented by $R_{51}$ is preferably an aliphatic group containing from 1 to 22 carbon atoms, and may have substituents or not, and furthermore, may have a chain form or a cyclic form. Preferably substituents therefor include an alkoxy group, an aryloxy group, an amino group, an acylamino group, a halogen atom, etc., each of which may further have a substituent(s). Specific examples of aliphatic groups useful for $R_{51}$ include an isopropyl group, an isobutyl group, a tert-butyl group, an isoamyl group, a tert-amyl group, a 1,1-dimethylbutyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an α-aminoisopropyl group, an α-(diethylamino)isopropyl group, an α-(succinimido)isopropyl group, an α-(phthalimido)isopropyl group, an α-(benzenesulfonamido)isopropyl group, etc.

In the case that $R_{51}$, $R_{52}$, or $R_{53}$ represents an aromatic group (especially a phenyl group), it may have a substituent. Such an aryl group as a phenyl group, etc. may be substituted with an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido group, alkyl-substituted succinimido group, etc., each containing 32 or less carbon atoms. The alkyl group therein may include an alkyl group which contains an aromatic group such as phenylene in its main chain. Further, a phenyl group represented by $R_{51}$, $R_{52}$, or $R_{53}$ may be substituted with an aryloxy group, an aryloxycarbonyl group, an arylcarbamoyl group, an arylamido group, an arylsulfamoyl group, an arylsulfonamido group, an arylureido group, etc., the aryl moiety of which may be substituted with one or more alkyl groups wherein the number of carbon atoms is from 1 to 22 in total.

Furthermore, a phenyl group represented by $R_{51}$, $R_{52}$, or $R_{53}$ may be substituted with an amino group which includes an amino group substituted with a lower alkyl group having from 1 to 6 carbon atoms, a hydroxyl group, a carboxy group, a sulfo group, a nitro group, a cyano group, a thiocyano group, or a halogen atom.

In addition, $R_{51}$, $R_{52}$, or $R_{53}$ may represent a substituent formed by condensing a phenyl group and another ring, such as a naphthyl group, a quinolyl group, an isoquinolyl group, a chromanyl group, a coumaranyl group, a tetrahydronaphthyl group, etc. These substituents may further have substituents in themselves.

In the case that $R_{51}$ represents an alkoxy group, the alkyl moiety thereof represents a straight chain or branched chain alkyl group having from 1 to 32 carbon atoms, preferably from 1 to 22 carbon atoms, an alkenyl group, a cyclic alkyl group or a cyclic alkenyl group, each of which may be substituted with a halogen atom, an aryl group,, an alkoxy group, etc.

In the case that $R_{51}$, $R_{52}$, or $R_{53}$ represents a heterocyclic group, the heterocyclic group is bonded to the carbon atom of the carbonyl group of the acyl moiety or the nitrogen atom of the amido moiety of an α-acylacetamido group through one of the carbon atoms forming the ring. Examples of such heterocyclic rings include thiophene, furan, pyran, pyrrole, pyrazole, pyridine, pyrazine, pyrimidine, pyridazine, indolizine, imidazole, thiazole, oxazole, triazine, thiadiazine, oxazine, etc. These rings may further have substituents on the individual rings.

In the above-described formula, $R_{55}$ represents a straight chain or branched chain alkyl group having from 1 to 32 carbon atoms, preferably from 1 to 22 carbon atoms (e.g., a methyl group, an isopropyl group, a tert-butyl group, a hexyl group, a dodecyl group, etc.), an alkenyl group (e.g., an allyl group, etc.), a cyclic alkyl group (e.g., a cyclopentyl group, a cyclohexyl group, a norbornyl group, etc.), an aralkyl group (e.g., a benzyl group, a β-phenylethyl group, etc.), a cyclic alkenyl group (e.g., a cyclopentenyl group, a cyclohexenyl group, etc.), etc., each of which groups may be substituted with a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, a mercapto group, etc.

$R_{55}$ may further represent an aryl group (e.g., a phenyl group, an α- or β-naphthyl group, etc.). The aryl group may have one or more substituents. Examples of the substituents include an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group, etc.

Furthermore, $R_{55}$ may represent a heterocyclic group (e.g., a 5-membered or 6-membered heterocyclic ring containing as a hetero atom a nitrogen atom, an oxygen atom or a sulfur atom, or a condensed ring thereof, with specific examples including a pyridyl group, a quinolyl group, a furyl group, a benzothiazolyl group, an oxazolyl group, an imidazolyl group, a naphthoxazolyl group, etc.), a heterocyclic group substituted with one or more substituents as defined for the above-described aryl group, an aliphatic acyl group, an aromatic acyl group, an alkylsulfonyl group, an arylsulfonyl group, an alkylcarbamoyl group, an arylcarbamoyl group, an alkylthiocarbamoyl group, or an arylthiocarbamoyl group.

In the above-described general formulae, $R_{54}$ represents a hydrogen atom, a straight chain or branched chain alkyl group having from 1 to 32 carbon atoms, preferably from 1 to 22 carbon atoms, an alkenyl group, a cyclic alkyl group, an aralkyl group, or a cyclic alkenyl group (each of which may have one or more substituents as defined for the above-described substituent $R_{55}$), an aryl group or a heterocyclic group (each of which also may have one or more substituents as defined for the above-described substituent $R_{55}$), an alkoxycarbonyl group (e.g., a methoxycarbonyl group, an ethoxycarbonyl group, a stearyloxycarbonyl group, etc.), an aryloxycarbonyl group (e.g., a phenoxycarbonyl group, a naphthoxycarbonyl group, etc.), an aralkyloxycarbonyl group (e.g., a benzyloxycarbonyl group, etc.), an alkoxy group (e.g., a methoxy group, an ethoxy group, a heptadecyloxy group, etc.), an aryloxy group (e.g., a phenoxy group, a tolyloxy group, etc.), an alkylthio group (e.g., an ethylthio group, a dodecylthio group, etc.), an arylthio group (e.g., a phenylthio group, an α-naphthylthio group, etc.), a carboxy group, an acylamino group (e.g., an acetylamino group, a 3-[(2,4-di-tert-amylphenoxy)acetamido]benzamido group, etc.), a diacylamino group, an N-alkylacylamino group (e.g., an N-methylpropionamido group, etc.), an N-arylacylamino group (e.g., an N-phenylacetamido group, etc.), a ureido group (e.g., a ureido group, an N-arylureido group, an N-alkylureido group, etc.), a urethane group, a thiourethane group, an arylamino group (e.g., a phenylamino group, an N-methylanilino group, a diphenylamino group, an N-acetylanilino group, a 2-chloro-5-tetradecanamidoanilino group, etc.), an alkylamino group (e.g., a n-butylamino group, a methylamino group, a cyclohexylamino group, etc.), a cycloamino group (e.g., a piperidino group, a pyrrolidino group, etc.), a heterocyclic amino group (e.g., a 4-pyridylamino group, a 2-benzoxazolylamino group, etc.), an alkylcarbonyl group (e.g., a methylcarbonyl group, etc.), an arylcarbonyl group (e.g., a phenylcarbonyl group, etc.), a sulfonamido group (e.g., an alkylsulfonamido group, an arylsulfonamido group, etc.), a carbamoyl group (e.g., an ethylcarbamoyl group, a dimethylcarbamoyl group, an N-methylphenylcarbamoyl group, an N-phenylcarbamoyl, etc.), a sulfamoyl group (e.g., an N-alkylsulfamoyl group, and N,N-dialkylsulfamoyl group, an N-arylsulfamoyl group, an N-alkyl-N-arylsulfamoyl group, an N,N-diarylsulfamoyl group, etc.), a cyano group, a hydroxy group, or a sulfo group.

In the above-described formulae, $R_{56}$ represents a hydrogen atom, or a straight chain or branched chain alkyl group having from 1 to 32 carbon atoms, and preferably from 1 to 22 carbon atoms, an alkenyl group, a cyclic alkyl group, an aralkyl group or a cyclic alkenyl group, each of which may have one or more substituents as defined for the above-described substituent $R_{55}$.

Further, $R_{56}$ may represent an aryl group or a heterocyclic group, each of which may have one or more substituents as defined for the above-described substituent $R_{55}$.

Furthermore, $R_{56}$ may represent a cyano group, an alkoxy group, an aryloxy group, a halogen atom, a carboxy group, an alkoxycarbonyl group, an aryloxycarbonyl group, an acyloxy group, a sulfo group, an acyl group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group or an N-acylanilino group.

In the above-described formulae, $R_{57}$, $R_{58}$, and $R_{59}$ each represents a group of a type which has been employed in conventional 4-equivalent type phenol or α-naphthol couplers. Specifically, $R_{57}$ represents a hydrogen atom, a halogen atom, an alkoxycarbonylamino group, an aliphatic hydrocarbon group, an N-arylureido group, an acylamino group, an —O—$R_{62}$ group or an —S—$R_{62}$ group (wherein $R_{62}$ is an aliphatic hydrocarbon group). When two or more $R_{57}$ groups are present in one molecule, they may be different from each other. The above-described aliphatic hydrocarbon groups include those having substituents. In the case that these substituents include an aryl group, the aryl group may have one or more substituents as defined for the above-described group $R_{55}$.

$R_{58}$ and $R_{59}$ each represents an aliphatic hydrocarbon group, an aryl group or a heterocyclic group. Either of them may be a hydrogen atom. The above-described groups for $R_{58}$ and $R_{59}$ may further have certain substituents. Furthermore, $R_{58}$ and $R_{59}$ may combine with each other and form a nitrogen-containing heterocyclic nucleus. More specifically, the above-described aliphatic hydrocarbon group includes both saturated and unsaturated groups, each of which may have a straight chain form, a branched chain form or a cyclic form. Preferred examples thereof include an alkyl group (e.g., a methyl group, an ethyl group, a propyl group, an isopropyl group, a butyl group, a tert-butyl group, an isobutyl group, a dodecyl group, an octadecyl group, a cyclobutyl group, a cyclohexyl group, etc.) and an alkenyl group (e.g., an allyl group, an octenyl group, etc.). The above-described aryl group includes a phenyl group, a naphthyl group, etc. Representatives of the above-described heterocyclic group include a pyridinyl group, a quinolyl group, a thienyl group, a piperidyl group, an imidazolyl group, etc. These aliphatic hydrocarbon groups, aryl groups, and heterocyclic groups may each be substituted with a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, a morpholino group, etc.

In the above-described formulae, l represents an integer of 1 to 4, m represents an integer of 1 to 3, and p represents an integer of 1 to 5.

In the above-described formula, $R_{60}$ represents an arylcarbonyl group, an alkanoyl group having from 2 to 32 carbon atoms, preferably from 2 to 22 carbon atoms, an arylcarbamoyl group, an alkanecarbamoyl group having from 2 to 32 carbon atoms, preferably from 2 to 22 carbon atoms, an alkoxycarbonyl group having from 1 to 32 carbon atoms, preferably from 1 to 22 carbon atoms or an aryloxycarbonyl group, which each may be substituted. Examples of the substituents include an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group, an aryl group, etc.

In the above-described formula, $R_{61}$ represents an arylcarbonyl group, an alkanoyl group having from 2 to 32 carbon atoms, preferably from 2 to 22 carbon atoms, an alkoxycarbonyl group having from 1 to 32 carbon atoms, preferably from 1 to 22 carbon atoms, an aryloxycarbonyl group, an alkylsulfonyl group having from 1 to 32 carbon atoms, preferably from 1 to 22 carbon atoms, an arylsulfonyl group, an aryl group or a 5-membered or 6-membered heterocyclic group (containing as a hetero atom, a nitrogen atom, an oxygen atom or a sulfur atom, with specific examples including a triazolyl group, an imidazolyl group, a phthalimido group, a succinimido group, a furyl group, a pyridyl group, a benzotriazolyl group, etc.), each of which may have one or more substituents as defined for the above-described substituent $R_{60}$.

Of the above-described coupler residues, those represented by formula (Cp-1) wherein $R_{51}$ represents a tert-butyl group or a substituted or unsubstituted aryl group and $R_{52}$ represents a substituted or unsubstituted aryl group, and those represented by formula (Cp-2) wherein $R_{52}$ and $R_{53}$ each represents a substituted or unsubstituted aryl group are preferred as yellow coupler residues.

As magenta coupler residues, preferred are those represented by formula (Cp-3) wherein $R_{54}$ represents an acylamino group, a ureido group, or an arylamino group and $R_{55}$ represents a substituted aryl group, those represented by formula (Cp-4) wherein $R_{54}$ represents an acylamino group, a ureido group, or an arylamino group and $R_{56}$ represents a hydrogen atom, and those represented by formula (Cp-5) or (Cp-6) wherein $R_{54}$ and $R_{56}$ each represents a straight chain or branched chain alkyl group, an alkenyl group, a cyclic alkyl group, an aralkyl group, or a cyclic alkenyl group.

As cyan couplers, those represented by formula (Cp-7) wherein $R_{57}$ represents an acylamino group or a ureido group at the 2-position, an acylamino group or an alkyl group at the 5-position, and a hydrogen atom or a chlorine atom at the 6-position, and those represented by formula (Cp-9) wherein $R_{57}$ represents a hydrogen atom, an acylamino group, a sulfonamido group or an alkoxycarbonyl group at the 5-position, $R_{58}$ represents a hydrogen atom and $R_{59}$ represents a phenyl group, an alkyl group, an alkenyl group, a cyclic alkyl group, an aralky group, or a cyclic alkenyl group are preferred.

As non-color forming coupler residues, those represented by formula (Cp-10) wherein $R_{56}$ represents an acylamino group, a sulfonamido group, or a sulfamoyl group, and those represented by formula (Cp-11) wherein $R_{60}$ and $R_{61}$ each represents an alkoxycarbonyl group, are preferred.

Further, by connecting any of the groups represented by $R_{51}$ to $R_{61}$, a polymeric compound including a bis compound or more may be formed. Moreover, a polymer composed of a monomer which is formed by containing an ethylenicallly unsaturated group in any of the groups represented by $R_{51}$ to $R_{61}$ or a copolymer composed of the coupler monomer described above and a non-color forming monomer may be employed.

When the coupler residue represented by A is a polymeric coupler residue, the coupler may be a polymer derived from a monomeric coupler represented by formula (Cp-12) described below, and have a recurring unit represented by formula (Cp-13) described below or may be a copolymer of the above-described monomer coupler and at least one of a non-color forming monomer having at least one ethylene group having no coupling ability with the oxidation product of an aromatic primary amine developing agent. In such cases, two or more kinds of the monomeric couplers may be copolymerized.

(Cp-12)

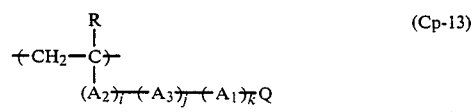

(Cp-13)

wherein R represents a hydrogen atom, a lower alkyl group having from 1 to 4 carbon atoms, or a chlorine atom; $A_1$ represents —CONR'—, —NR'CONR'—, —NR'COO—, —COO—, —SO$_2$—, —CO—, —NR'CO—, —SO$_2$NR'—, —NR'SO$_2$—, —OCO—, —OCONR'—, —NR'— or —O—; $A_2$ represents —CONR'— or —COO—; R' represents a hydrogen atom, an aliphatic group or an aryl group, when two or more R' groups are present in one molecule, they may be the same or different; $A_3$ represents a substituted or unsubstituted alkylene group having from 1 to 10 carbon atoms, a substituted or unsubstituted aralkylene group, or a substituted or unsubstituted arylene group.

The alkylene group may be a straight chain or branched alkylene group, and includes, for example, a methylene group, a methylmethylene group, a dimethylmethylene group, a dimethylene group, a trimethylene group, a tetramethylene group, a pentamethylene group, a hexamethylene group, a decylmethylene group, etc. Examples of the aralkylene group include a benzylidene group, etc. Examples of the arylene group include a phenylene group, a naphthylene group, etc.

Q in the above described formulae represents a coupler residue which is connected through any of the groups represented by $R_{51}$ to $R_{61}$ in formulae (Cp-1) to (Cp-11).

Also, i, j, and k each represents 0 or 1.

Examples of a substituent for the alkylene group, aralkylene group, or arylene group represented by $A_3$ include an aryl group (e.g., a phenyl group, etc., a nitro group, a hydroxy group, a cyano group, a sulfo group, an alkoxy group (e.g., a methoxy group, etc.), an aryloxy group (e.g., a phenoxy group, etc.), an acyloxy group (e.g., an acetoxy group, etc.), an acylamino group (e.g., an acetylamino group, etc.), a sulfonamido group (e.g., a methanesulfonamido group, etc.), a sulfamoyl group (e.g., a methylsulfamoyl group, etc.), a halogen atom (e.g., a fluorine atom, a chlorine atom, a bromine atom, etc.), a carboxy group, a carbamoyl group (e.g., a methylcarbamoyl group, etc.), an alkoxycarbonyl group (e.g., a methoxycarbonyl group, etc.), a sulfonyl group (e.g., a methylsulfonyl group, etc.), etc. When the group represented by $A_3$ has two or more substituents, they may be the same or different.

As the non-color forming ethylenic monomer which does not cause coupling with the oxidation product of an aromatic primary amine developing agent, there are an acrylic acid, such as acrylic acid, α-chloroacrylic acid, α-alkylacrylic acid, an ester or amide derived from an acrylic acid, methylenebisacrylamide, a vinyl ester, an acrylonitrile, an aromatic vinyl compound, a maleic acid derivative, a vinylpyridine, etc. In this case, two or more non-color-forming ethylenically unsaturated monomers can be used.

In formula (I), preferred examples of groups represented by the combination of X and Y are illustrated by formulae (II), (III), (IV), (V), (VI), (VII), (VIII), and (IX)

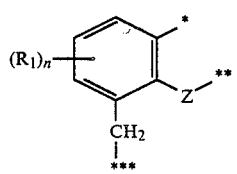
(II)

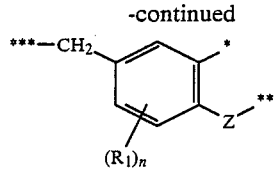
(III)

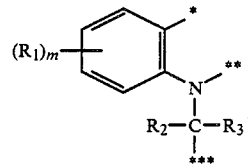
(IV)

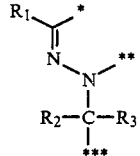
(V)

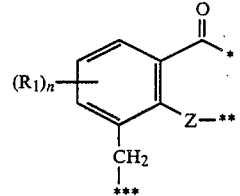
(VI)

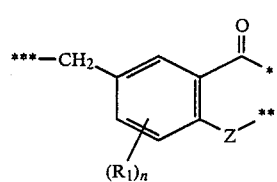
(VII)

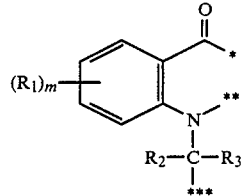
(VIII)

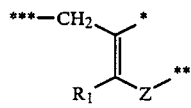
(IX)

wherein a bond indicated by * denotes the position at which the group is connected to CH of formula (I), a bond indicated by  denotes the position at which the group is connected to the carbonyl group of formula (I), and a bond indicated by * denotes the position at which the group is connected to PUG of formula (I); $R_1$ represents a hydrogen atom or a group capable of being substituted on an aromatic ring. Preferred examples of $R_1$ include a hydrogen atom, a halogen atom, an aliphatic group, an aromatic group, a heterocyclic group, $R_4O$—, $R_4S$—, $R_4OOC$—, $R_4CO$—, $R_4CONH$—, $R_4SO_2NH$—, $R_4NHSO_2$—, $R_4NHCO$—, a hydroxy group, a nitro group, a cyano group, $R_4NHCONH$—, $R_4COO$— or a carboxy group, etc., wherein $R_4$ represents an aliphatic group, an aromatic group, or a heterocyclic group.

In the above-described formulae, Z represents —O—, —S—, or

wherein $R_5$ represents $R_4$, $R_4CO-$, $R_4SO_2-$ or $R_4NHCO-$.

n represents an integer from 1 to 3, and m represents an integer from 1 to 4. When n or m represents 2 or more, the two or more $R_1$ groups may be the same or different.

In the above-described formulae, $R_2$ and $R_3$ each represents a hydrogen atom or a group capable of being substituted at a methylene group. Preferred examples of $R_2$ or $R_3$ include a hydrogen atom, $R_4OOC-$, $R_4CO-$, an aromatic group, a heterocyclic group, etc.

The aliphatic group represented by $R_1$, $R_2$, $R_3$, $R_4$, or $R_5$ includes a straight chain, branched chain or cyclic, saturated or unsaturated, substituted or unsubstituted aliphatic group having from 1 to 30 carbon atoms, and preferably from 1 to 18 carbon atoms.

The aromatic group represented by $R_1$, $R_2$, $R_3$, $R_4$ or $R_5$ include a substituted or unsubstituted aromatic group having from 6 to 10 carbon atoms, and preferably represents a substituted or unsubstituted phenyl group.

The heterocyclic group represented by $R_1$, $R_2$, $R_3$, $R_4$, or $R_5$ include a 4-membered, 5-membered, 6-membered, 7-membered, or 8-membered heterocyclic group containing at least one hetero atom selected from a nitrogen atom, an oxygen atom and a sulfur atom. Examples of the heterocyclic groups include a 2-pyridyl group, a 4-imidazolyl group, 1-pyrrolidino group, a 2-furyl group, a 4-quinolyl group, etc.

Of the groups represented by formulae (II) to (IX), those represented by formula (IV) are particularly preferred.

The photographically useful group represented by PUG in formula (I) preferably includes a group containing a development inhibitor, a development accelerator, a silver halide solvent, a dye, a fogging agent, a developing agent, a coupler, a fixing accelerator, or a fixing inhibitor, etc.

Examples of preferred photographically useful groups include the photographically useful groups as described in U.S. Pat. No. 4,248,962 (those represented by PUG in the general formula of the patent) and the fogging agents as described in Japanese Patent Application (OPI) No. 170840/84 (the portions of cleavage groups capable of being released from couplers in the patent).

The fogging agents described in Japanese Patent Application (OPI) No. 170840/84 are represented by the formula

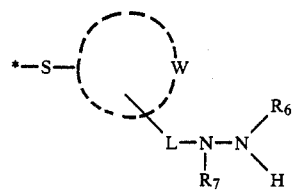

wherein a bond indicated by * denotes the position at which the group is connected; W represents a monocyclic or condensed heterocyclic ring consisting of a carbon atom and a nitrogen atom; L represents a divalent linking group; $R_7$ represents a hydrogen atom or an alkoxycarbonyl group; and $R_6$ represents a hydrogen atom, an acyl group, a sulfonyl group, an alkoxycarbonyl group, a carbamoyl group, a sulfamoyl group, a thioacyl group, a thiocarbamoyl group, an alkyl group or an aryl group.

Particularly preferred PUG include a development inhibitor such as a 5-aryltetrazolylthio group, a 5-aliphatic group substituted tetrazolylthio group, a benzimidazolylthio group, a benzothiazolylthio group, a benzoxazolylthio group, a benzotriazolyl group, a benzindazolyl group, etc.

The above-described development inhibitors include those having a substituent defined for $R_1$ to $R_5$ in which the total number of carbon atoms included in the substituent(s) is 22 or less, and preferably 10 or less.

The amount of the compound added according to the present invention may be varied depending on the particular structure and purposes of the compound. However, it is preferably employed in a range from $1 \times 10^{-6}$ to 1 mol, and particularly preferably from $1 \times 10^{-3}$ to $5 \times 10^{-1}$ mol, per mol of silver present in the same layer or an adjacent layer.

The compound according to the present invention can be used alone or together with known couplers in a layer. In the case of use together with other color image forming couplers, a ratio of the compound according to the present invention to other color image forming couplers (the compound according to the present invention/other color image forming couplers) is generally from 0.1/99.9 to 90/10, and preferably from 1/99 to 50/50.

Specific examples of the compound according to the present invention are set forth below, but the present invention should not be construed as being limited thereto.

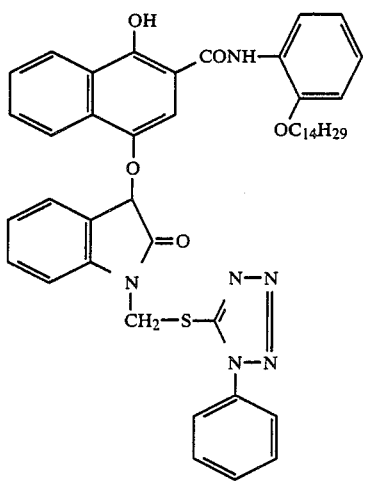
(1)
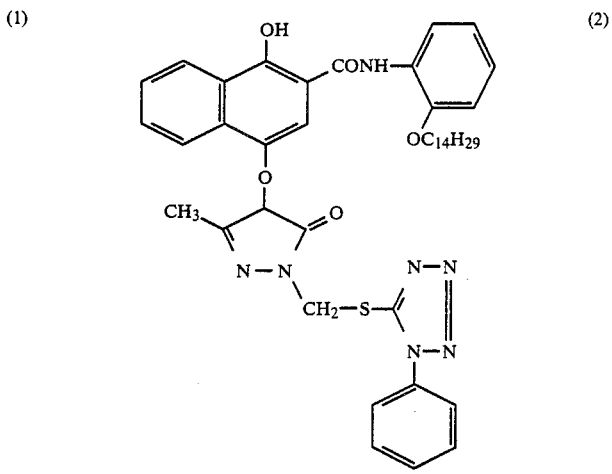
(2)
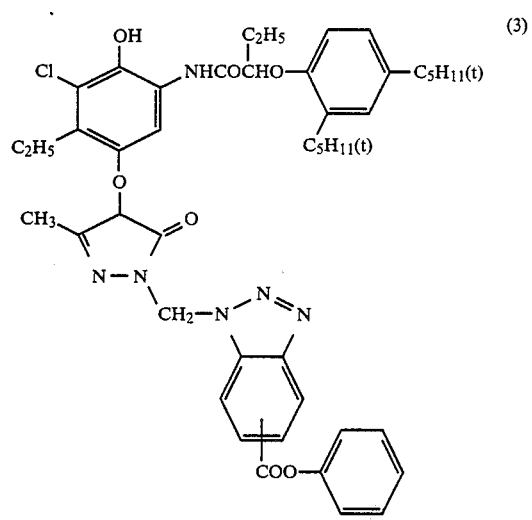
(3)
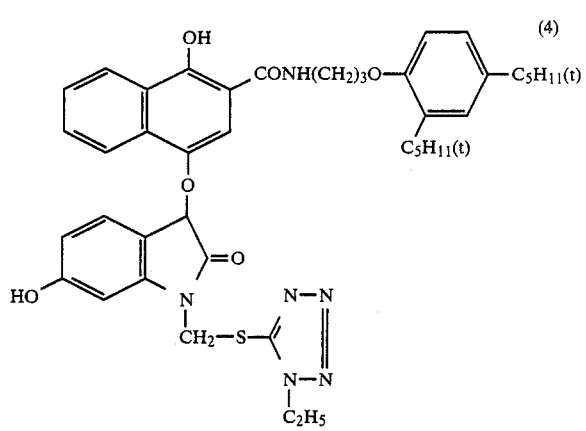
(4)
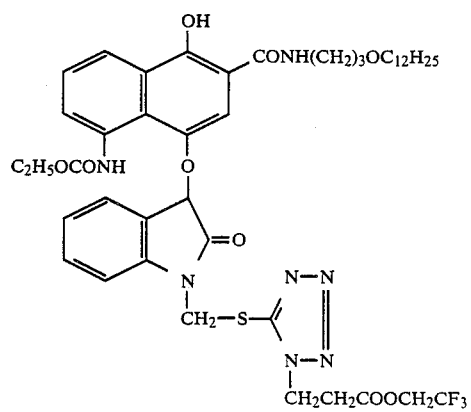
(5)
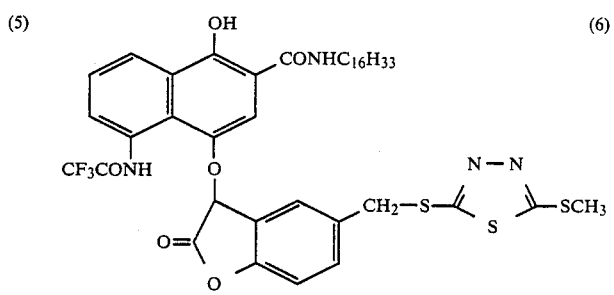
(6)

-continued
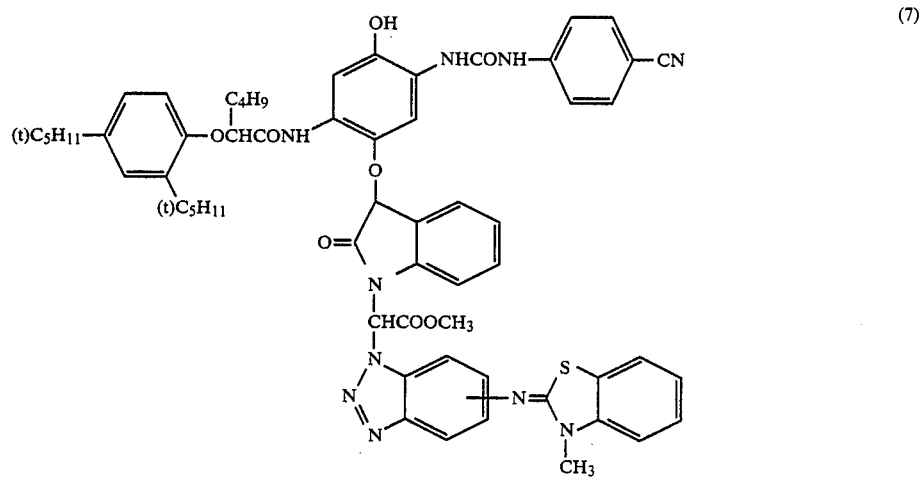
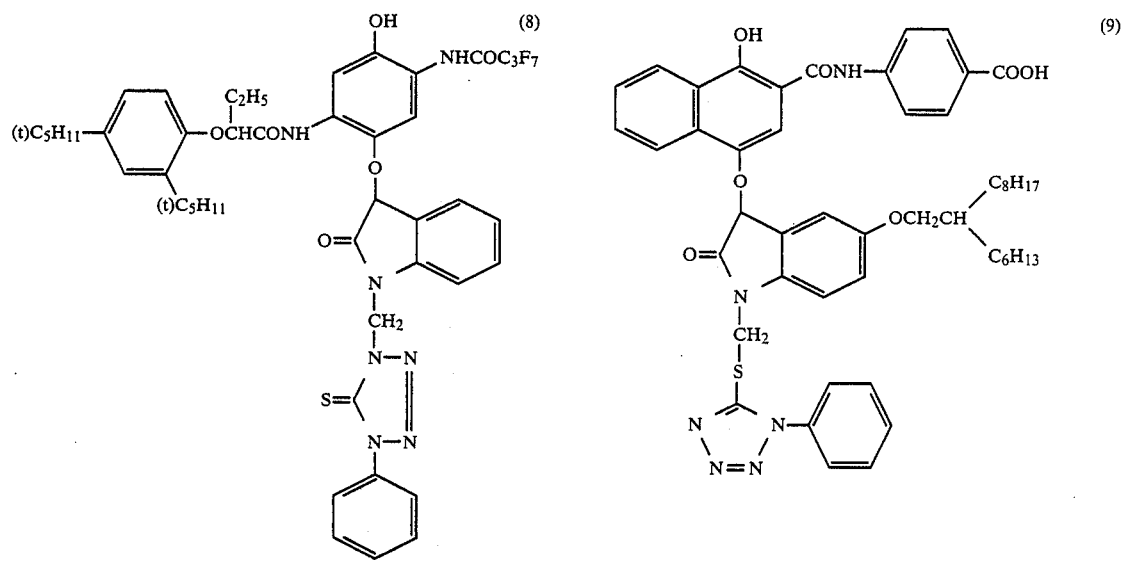
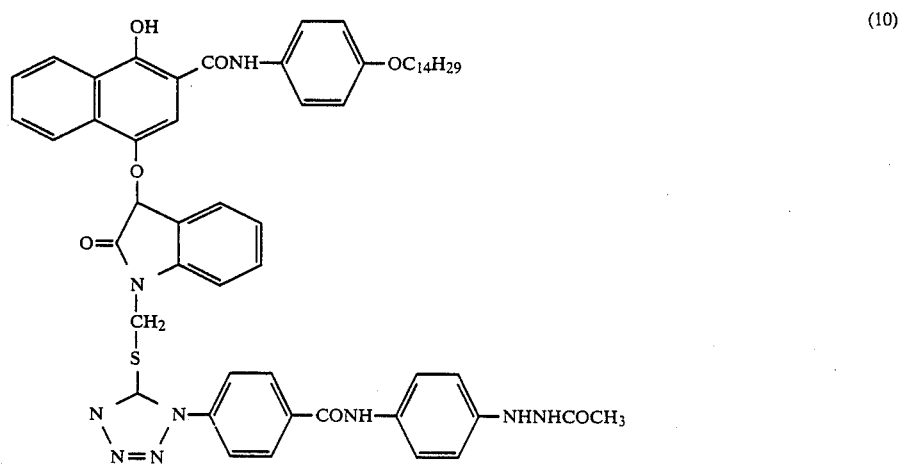

-continued
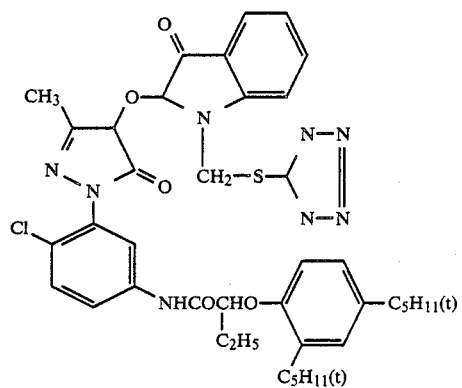
(11)
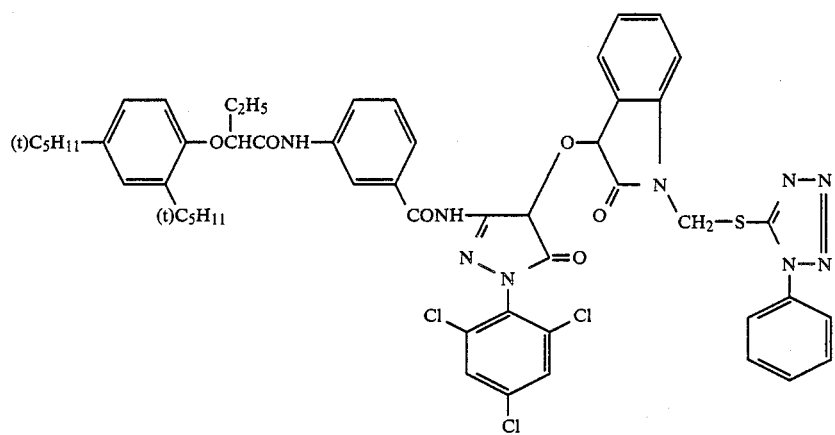
(12)
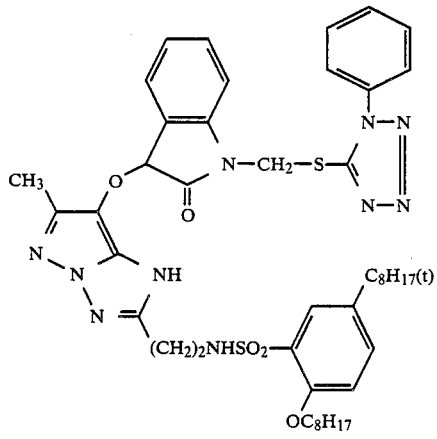
(13)
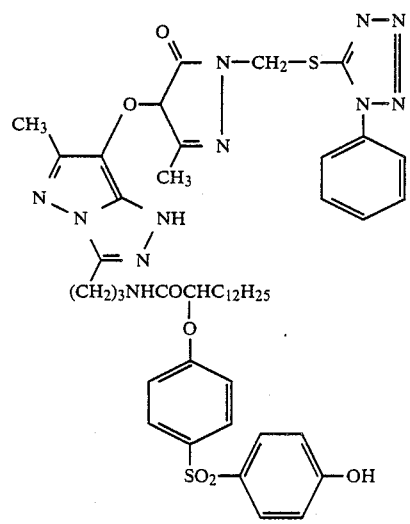
(14)

-continued
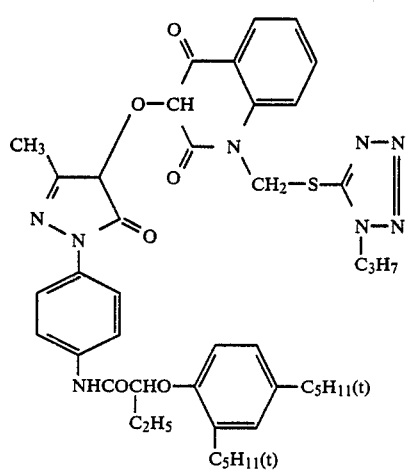
(15)
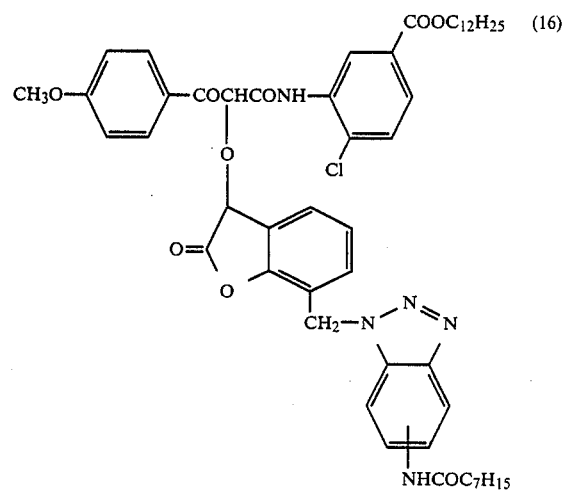
(16)
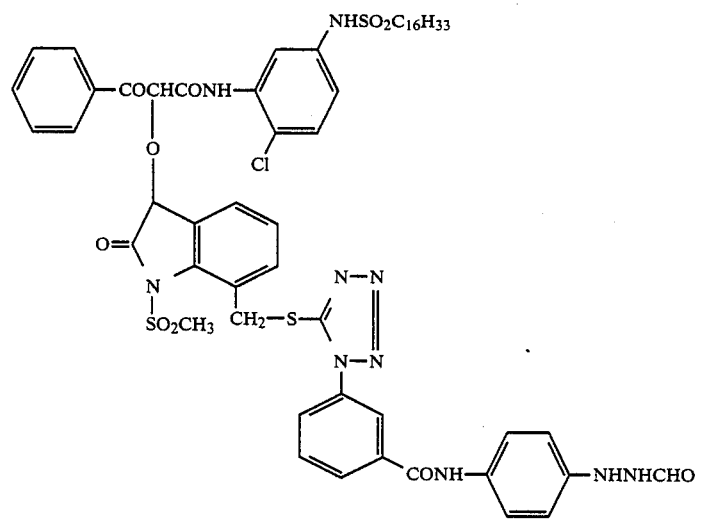
(17)
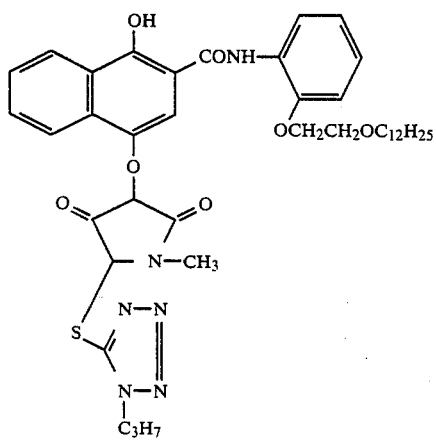
(18)
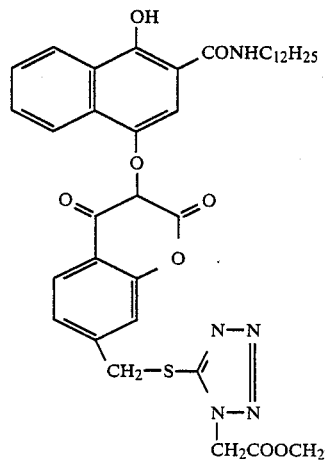
(19)

(20)
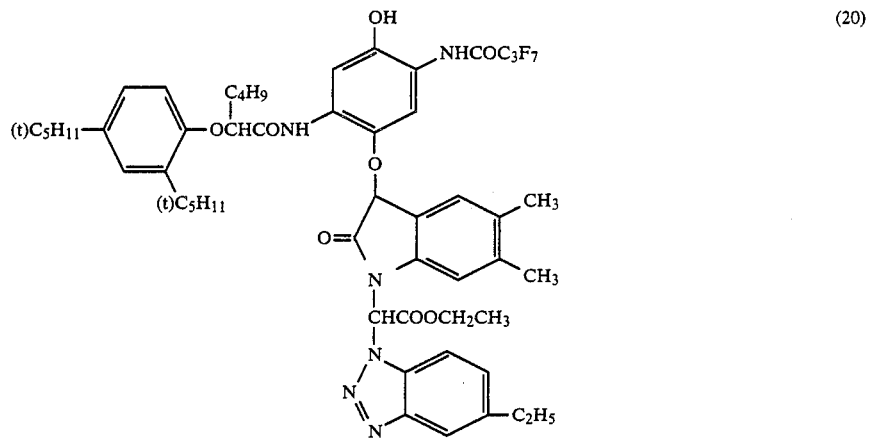
(21)
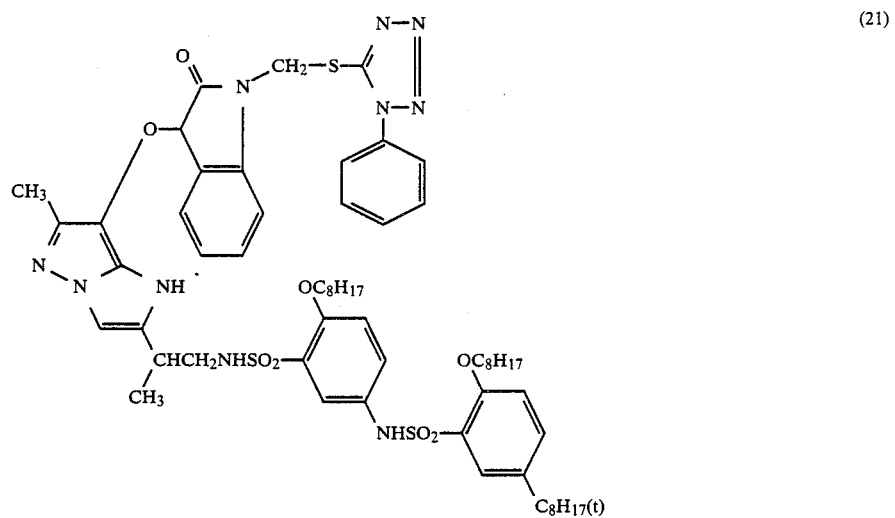
(22)
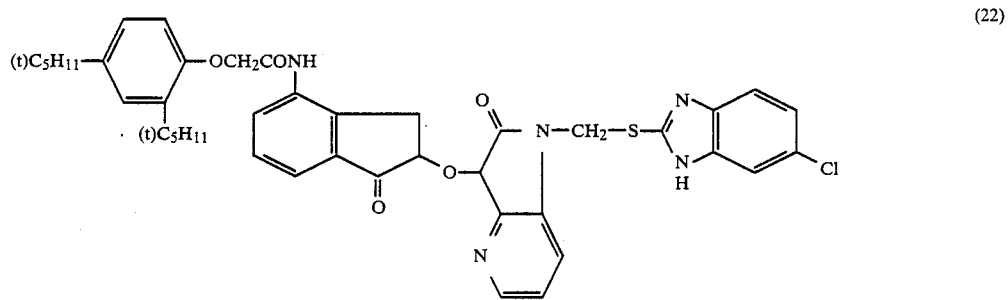

-continued (23)

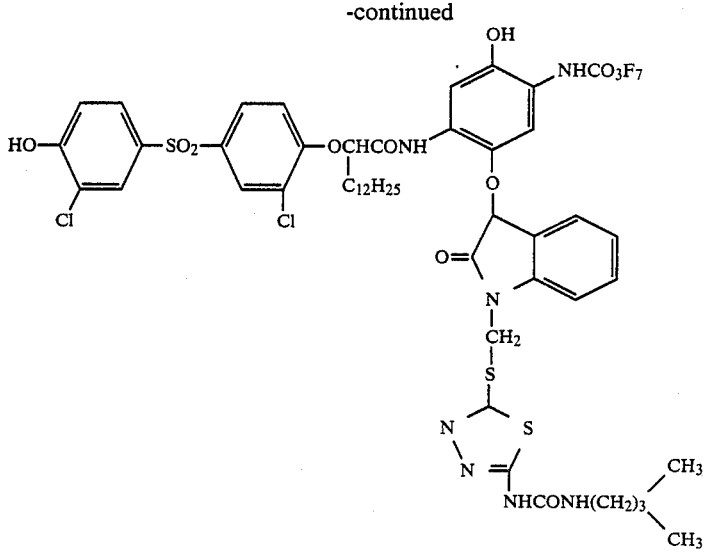

A synthesis examples of the typical compound according to the present invention is specifically set forth below. Other compounds may be synthesized in a similar manner.

SYNTHESIS EXAMPLE

Synthesis of Compound (1)

45 g of isatin was mixed with 150 ml of acetic acid; to the mixture was added 60 g of formalin (37 wt% formaldehyde solution), and the mixture was stirred at room temperature for 5 hours. The solvent was distilled off under reduced pressure, and to the residue was added 200 ml of chloroform. 23 ml of thionyl chloride was added to the mixture, and the mixture was allowed to stand overnight at room temperature. The solvent was removed under reduced pressure, and to the residue was added 200 ml of chloroform. To the solution were added 54.5 g of 1-phenyl-5-mercaptotetrazole and 31.6 g of triethylamine and the mixture was reacted at room temperature for 3 hours. The reaction mixture was subjected to after-treatment in a conventional manner, followed by recrystallization from a solvent mixture of ethyl acetate and hexane to obtain 53.2 g of 1-(1-phenyl-tetrazolyl-5-thiomethyl)isatin.

53.2 g of the isatin derivative thus obtained was reduced according to the method as described in Berichte, Vol. 44, page 1455 (1911) to synthesize a dioxyindole derivative. Then, using methyl chloride in the presence of pyridine in a conventional manner, a mesylate was synthesized.

38.6 g of the mesylate obtained above and 18.9 g of 1,4-dihydroxy-2-naphthoic acid were added to 100 ml of N,N-dimethylformamide and to the mixture was added dropwise 35.8 g of a methanol solution containing 10 g of sodium methoxide dissolved therein under a nitrogen atmosphere. After being subjected to reaction at room temperature for 3 hours, 200 ml of water was added to the mixture. Upon gradually added hydrochloric acid the crystals were deposited which were separated by filtration to obtain 23.6 g of the intermediate (naphthoic acid derivative).

23.6 g of the intermediate obtained above and 13.7 g of 2-tetradecyloxyaniline were added to 150 ml of N,N-dimethylformamide and to the mixture was added dropwise a solution containing 9.3 g of N,N'-dicyclohexylcarbodiimide dissolved in 20 ml of acetonitrile at room temperature. The mixture was subjected to reaction for 3 hours and aftertreatment in a conventional manner, followed by recrystallization from a solvent mixture of ethyl acetate and hexane to obtain 25.3 g of Compound (1).

In the photographic emulsion layer used in the photographic light-sensitive material according to the present invention, any of silver bromide, silver iodobromide, silver iodochlorobromide, silver chlorobromide, and silver chloride may be used as the silver halide. A preferred halide is silver iodobromide or silver iodochlorobromide each containing 30 mol% or less of silver iodide. Silver iodobromide containing from 2 mol% to 25 mol% of silver iodide is particularly preferred.

Silver halide grains in the photographic emulsion may have a regular crystal structure, for example, a cubic, octahedral or tetradecahedral structure, etc., an irregular crystal structure, for example, a spherical structure, etc., a crystal defect, for example, a twinned plane, etc., or a composite structure thereof.

The grain size of silver halide may be varied and include from fine grains having an average grain diameter of 0.1 micron or less to large size grains having an average grain diameter of 10 microns of projected area. In the case where the silver halide is not a spherical form, the average grain diameter means an average diameter of spherical grains calculated as having the same volume as that of such non-spherical grains. Further, a mono-dispersed emulsion having a narrow grain size distribution and a poly-dispersed emulsion having a broad grain size distribution may be used.

The silver halide photographic emulsion used in the present invention can be prepared using known methods, for example, those as described in Research Disclosure, No. 17643 (December 1978), pages 22 to 23, "I. Emulsion Preparation and Types" and ibid., No. 18716 (November 1979), page 648, etc.

The photographic emulsion as used in the present invention can be prepared in any suitable manner, for example, by the methods as described in P. Glafkides, Chimie et Physique Photographique, pp. 329–425, Paul Montel (1967), G. F. Duffin Photographic Emulsion Chemistry, pp. 57–82, The Focal Press (1966), and V. L. Zelikman et al., Making and Coating Photographic Emulsion, pp. 69–87, The Focal Press (1964). That is, any of an acid process, a neutral process, an ammonia process, etc., can be employed.

Soluble silver salts and soluble halogen salts can be reacted by techniques such as a single jet process, a double jet process, and a combination thereof. In addition, there can be employed a method (so-called reversal mixing process) in which silver halide particles are formed in the presence of an excess of silver ions.

As one system of the double jet process, a so-called controlled double jet process in which the pAg in a liquid phase where silver halide is formed is maintained at a predetermined level can be employed. This process can produce a silver halide emulsion in which the crystal form is regular and the grain size is nearly uniform.

Two or more kinds of silver halide emulsions which are prepared separately may be used as a mixture.

Silver halide emulsions composed of regular grains as described above can be obtained by controlling pAg and pH during the step of formation of silver halide grains. The details thereof are described, for example, in *Photographic Science and Engineering*, Vol. 6, pp. 159-165 (1962), *Journal of Photographic Science*, Vol. 12, pp. 242-251 (1964), U.S. Pat. No. 3,655,394, and British Pat. No. 1,413,748, etc.

Representative mono-dispersed emulsions are those comprising silver halide grains having an average grain size of about 0.1 micron or more and at least about 95% by weight of the total silver halide grains having a size within the range of ±40% of the average grain size. In the present invention, it is preferred to employ a mono-dispersed emulsion comprising silver halide grains having an average grain size of from 0.25 microns to 2 microns and at least 95% by weight or by number of particles of the total silver halide grains having a size within the range of ±20% of the average grain size. Methods for preparation of such mono disperse emulsion are described in U.S. Pat. Nos. 3,574,628 and 3,655,394, British Pat. No. 1,413,748, etc. Further, mono disperse emulsions are described in Japanese Patent Application (OPI) Nos. 8600/73, 39027/76, 83097/76, 137133/78, 48521/79, 99419/79, 37635/83 and 49938/83, etc. can be preferably employed in the present invention.

Further, tabular silver halide grains having an aspect ratio of about 5 or more can be employed in the present invention. The tabular grains may be easily prepared by the method as described in Gutoff, *Photographic Science and Engineering*, Vol. 14, pp. 248-257 (1970), U.S. Pat. Nos. 4,434,226, 4,414,310, 4,433,048 and 4,439,520, British Pat. No. 2,112,157, etc. In the case of employing the tabular silver halide grains, it is described in detail that many advantages, for example, increase in spectral sensitizing efficiency with a sensitizing dye, improvement in graininess and improvement in sharpness, etc., are obtained in U.S. Pat. No. 4,434,226, etc., mentioned above.

Crystal structure of silver halide grains may be uniform, composed of different halide compositions between the inner portion of the outer portion, or may have a layer structure. Examples of such emulsion grains are described in British Pat. No. 1,027,146, U.S. Pat. Nos. 3,505,068 and 4,444,877, and Japanese Patent Application (OPI) No. 143331/85, etc.

Further, silver halide emulsions in which silver halide grains having different compositions are connected upon epitaxial junctions or silver halide emulsions in which silver halide grains are connected with compounds other than silver halide such as silver thiocyanate, lead oxide, etc. may also be employed. Examples of these emulsion grains are described in U.S. Pat. Nos. 4,094,684, 4,142,900 and 4,459,353, British Pat. No. 2,038,792, U.S. Pat. Nos. 4,349,622, 4,395,478, 4,433,501, 4,463,087, 3,656,962 and 3,852,067, Japanese Patent Application (OPI) No. 162540/84, etc.

Moreover, a mixture of grains having a different crystal structure may be used.

The photographic emulsions used in the present invention are usually conducted with physical ripening, chemical ripening and spectral sensitization. Various kinds of additives which can be employed in these steps are described in *Research Disclosure*, No. 17643 (December 1978) and ibid., No. 18716 (November 1979) as mentioned above and concerned items thereof are summarized in the table shown below.

Further, known photographic additives which can be used in the present invention are also described in the above mentioned *Research Disclosure* and concerned items thereof are summarized in the table below.

| Kind of Additives | RD 17643 | RD 18716 |
|---|---|---|
| 1. Chemical Sensitizers | Page 23 | Page 648, right column |
| 2. Sensitivity Increasing Agents | | " |
| 3. Spectral Sensitizers and Super Sensitizers | Pages 23 to 24 | Page 648, right column to Page 649, right column |
| 4. Antifoggants and Stabilizers | Pages 24 to 25 | Page 649, right column |
| 5. Light-Absorbers, Filter Dyes and Ultraviolet Ray Absorbers | Pages 25 to 26 | Page 649, right column to Page 650, left column |
| 6. Antistain Agents | Page 25, right column | Page 650, left column to right column |
| 7. Hardeners | Page 26 | Page 651, left column |
| 8. Binders | Page 26 | " |
| 9. Plasticizers and Lubricants | Page 27 | Page 650, right column |
| 10. Coating Aids and Surfactants | Pages 26 to 27 | " |
| 11. Antistatic Agents | Page 27 | " |

In the present invention, various color couplers can be employed. Specific examples of such couplers are described in the patents cited in *Research Disclosure*, No. 17643, "VII-C" to "VII-G" as mentioned above. As dye forming couplers, couplers capable of providing three primary colors (i.e., yellow, magenta, and cyan) in the subtractive process upon color development are important.

Specific examples of preferred diffusion-resistant, four-equivalent or two-equivalent couplers are described in the patents cited in *Research Disclosure*, No. 17643, "VII-C" and "VII-D" as mentioned above. In addition, couplers as described below are preferably employed in the present invention.

As typical yellow couplers used in the present invention, hydrophobic acylacetamide type couplers having a ballast group are exemplified. Specific examples thereof are described in U.S. Pat. Nos. 2,407,210, 2,875,057 and 3,265,506, etc. In the present invention two-equivalent yellow couplers are preferably employed.

Typical examples of two-equivalent yellow couplers include yellow couplers of oxygen atom releasing type as described in U.S. Pat. Nos. 3,408,194, 3,447,928, 3,933,501 and 4,022,620, etc. and yellow couplers of nitrogen atom releasing type as described in Japanese Patent Publication No. 10739/83, U.S. Pat. Nos. 4,401,752 and 4,326,024, *Research Disclosure*, No. 18053 (April 1979), British Pat. No. 1,425,020, West German Patent Application (OLS) Nos. 2,219,917, 2,261,361, 2,329,587 and 2,433,812, etc. α-Pivaloylacetanilide type couplers are characterized by fastness, particularly light fastness, of dyes formed, and α-benzoylacetanilide type couplers are characterized in that they provide a high color density.

As magenta couplers used in the present invention, hydrophobic indazolone type couplers, cyanoacetyl type couplers, and preferably 5-pyrazolone type couplers and pyrazoloazole type couplers each having a ballast group are exemplified. Of 5-pyrazolone type couplers, those substituted with an arylamino group or an acylamino group at the 3-position thereof are preferred in view of hue and color density of dyes formed. Typical examples thereof are described in U.S. Pat. Nos. 2,311,082, 2,343,703, 2,600,788, 2,908,573, 3,062,653, 3,152,896 and 3,936,015, etc. As releasing groups for two-equivalent 5-pyrazolone type couplers, nitrogen atom releasing groups as described in U.S. Pat. No. 4,310,619 and arylthio groups as described in U.S. Pat. No. 4,351,897 are particularly preferred. Further, 5-pyrazolone type couplers having a ballast group as described in European Pat. No. 73,636 are advantageous since they provide a high color density.

Examples of pyrazoloazole type couplers include pyrazolobenzimidazole as described in U.S. Pat. No. 3,369,879, and preferably pyrazolo[5,1-C][1,2,4]triazoles as described in U.S. Pat. No. 3,725,067, pyrazolotetrazoles as described in *Research Disclosure*, No. 24220 (June 1984) and Japanese Patent Application (OPI) No. 33552/85 and pyrazolopyrazoles as described in *Research Disclosure*, No. 24230 (June 1984) and Japanese Patent Application (OPI) No. 43659/85. Imidazo[1,2-b]pyrazoles as described in U.S. Pat. No. 4,500,630 are preferred and pyrazolo[1,5-b][1,2,4]triazoles as described in U.S. Pat. No. 4,540,654 are particularly preferred in view of less yellow subsidiary absorption and light fastness of dyes formed.

As cyan couplers used in the present invention, hydrophobic and diffusion-resistant naphthol type and phenol type couplers are exemplified. Typical examples thereof include naphthol type couplers as described in U.S. Pat. No. 2,474,293 and preferably oxygen atom releasing type two-equivalent naphthol type couplers as described in U.S. Pat. Nos. 4,052,212, 4,146,396, 4,228,233 and 4,296,200, etc. Specific examples of phenol type couplers are described in U.S. Pat. Nos. 2,369,929, 2,801,171, 2,772,162 and 2,895,826, etc.

Cyan couplers fast to humidity and temperature are preferably used in the present invention. Typical examples thereof include phenol type cyan couplers having an alkyl group more than a methyl group at the meta-position of the phenol nucleus as described in U.S. Pat. No. 3,772,002, 2,5-diacylamino-substituted phenol type couplers as describe in U.S. Pat. Nos. 2,772,162, 3,758,308, 4,126,396, 4,334,011 and 4,327,173, West German Patent Application (OLS) No. 3,329,729, and European Pat. No. 121,365, etc., and phenol type couplers having a phenylureido group at the 2-position thereof and an acylamino group as the 5-position thereof, as described in U.S. Pat. Nos. 3,446,622, 4,333,999, 4,451,559, 4,427,767, etc.

It is preferred to conduct masking by using colored couplers together in color photographic light-sensitive materials for photography in order to correct undesirable absorptions of dyes formed. Typical examples of colored couplers include yellow-colored magenta couplers as described in U.S. Pat. No. 4,163,670 and Japanese Patent Publication No. 39413/82, etc. and magenta-colored cyan couplers as described in U.S. Pat. Nos. 4,004,929 and 4,138,258 and British Pat. No. 1,146,368, etc. Other examples of useful colored couplers are described in *Research Disclosure*, No. 17643, "VII-G" as mentioned above.

Further, couplers capable of forming appropriately diffusible dyes can be used together in order to improve graininess. Specific examples of such types of magenta couplers are described in U.S. Pat. No. 4,366,237 and British Pat. No. 2,125,570, etc., and those of yellow, magenta and cyan couplers are described in European Pat. No. 96,570 and West German Patent Application (OLS) No. 3,234,533, etc.

Dye forming couplers and the above described special couplers may form polymers including dimers or oligomers. Typical examples of polymerized dye forming couplers are described in U.S. Pat. Nos. 3,451,820 and 4,080,211, etc. Specific examples of polymerized magenta couplers are described in British Pat. No. 2,102,173 and U.S. Pat. No. 4,409,320, etc. and two-equivalent couplers as described in U.S. Pat. No. 4,367,282, etc.

Couplers capable of releasing a photographically useful residue during the course of coupling can be also employed preferably in the present invention. Specific examples of useful DIR couplers capable of releasing a development inhibitor are described in the patents cited in *Research Disclosure*, No. 17643, "VII-F" mentioned above.

Of DIR couplers, those of deactivation type in a developing solution as represented by Japanese Patent Application (OPI) No. 151944/82, those of timing type as represented by U.S. Pat. No. 4,248,962 and Japanese Patent Application (OPI) No. 154234/82 and those of reactive type as represented by Japanese Patent Application (OPI) No. 184248/85 are preferred to employ them in combination with the present invention. Further, DIR couplers of deactivation type in a developing solution as described in Japanese Patent Application (OPI) Nos. 151944/82, 217932/83, 218644/85, 225156/85 and 233650/85, etc. and DIR couplers of reactive type as described in Japanese Patent Application (OPI) No. 184248/85, etc., are particularly preferred.

Suitable supports which can be used in the present invention are described, for example, in *Research Disclosure*, No. 17643, page 28 and ibid., No. 18716, page 647, right column to page 648, left column, as mentioned above.

The color photographic light-sensitive material according to the present invention can be subjected to development processing in a conventional manner as described in *Research Disclosure*, No. 17643, pages 28 to 29 and ibid., No. 18716, page 651, left column to right column.

After a development, bleach-fixing, or fixing step, the color photographic material according to the present invention is usually subjected to a water washing process or a stabilizing process.

The water washing step is generally conducted by a countercurrent water washing step using two or more tanks in order to reduce the amount of water used. As a stabilizing processing, a representative example is a multistage countercurrent stabilizing process as described in Japanese Patent Application (OPI) No. 8543/82, in place of the water washing step. In this step two to nine tanks of counter-current bath is necessary. To the stabilizing bath various kinds of compounds can be added for the purpose of stabilizing images formed. Representative examples of the additives include various buffers (for example, borates, metaborates, borax, phosphates, carbonates, potassium hydroxide, sodium hydroxide, aqueous ammonia, monocarboxylic acids, dicarboxylic acids, polycarboxylic acids, etc., being used in combination) for the purpose of adjusting pH of layers (for example, pH of 3 to 8), and a formalin, etc. In addition, various additives, for example, water softeness (for example, inorganic phosphoric acids, aminopolycarboxylic acids, organic phosphoric acids, aminopolyphosphonic acids, phosphonocarboxylic acids, etc.), sterilizers (for example, benzoisothiazolinones, isothiazolones, 4-thiazolinebenzimidazoles, halogenated phenols, etc.), surface active agents, fluorescent whitening agents, hardeners, etc., may be employed, if desired. Two or more compounds for the same or different purposes may be employed together.

Further, it is preferred to add various ammonium salts such as ammonium chloride, ammonium nitrate, ammonium sulfate, ammonium phosphate, ammonium sulfite, ammonium thiosulfate, etc., as pH adjusting agent for layers after development processing.

The present invention can be applied to various color photographic light-sensitive materials. Representative examples include color negative films for general use or movies, color reversal films for slides or television, color paper, color positive films, color reversal paper, etc. The present invention may also be applied to black and white photographic light-sensitive materials utilizing a mixture of three color couplers as described in *Research Disclosure*, No. 17123 (July 1978), etc.

The present invention is now illustrated in greater detail with reference to the following examples, but it should be understood that these examples do not limit the present invention.

EXAMPLE 1

On a polyethylene terephthalate film support were coated layers having the compositions set forth below to prepare a multilayer color photographic light-sensitive material.

First Layer: Antihalation Layer
  A gelatin layer containing black colloidal silver
Second Layer: Intermediate Layer
  A gelatin layer containing a dispersion of 2,5-di-tert-octylhydroquinone
Third Layer: First Red-Sensitive Emulsion Layer
  A silver iodobromide emulsion (iodide content: 5 mol%), silver coated amount: 1.6 g/m$^2$
    Sensitizing Dye I: $4.5 \times 10^{-4}$ mol per mol of silver
    Sensitizing Dye II: $1.5 \times 10^{-4}$ mol per mol of silver
    Coupler EX-1: 0.03 mol per mol of silver
    Coupler EX-3: 0.003 mol per mol of silver
Fourth Layer: Second Red-Sensitive Emulsion Layer
  A silver iodobromide emulsion (iodide content: 10 mol%), silver coated amount: 1.4 g/m$^2$
    Sensitizing Dye I: $3 \times 10^{-4}$ mol per mol of silver
    Sensitizing Dye II: $1 \times 10^{-4}$ mol per mol of silver
    Coupler EX-1: 0.002 mol per mol of silver
    Coupler EX-2: 0.02 mol per mol of silver
    Coupler EX-3: 0.0016 mol per mol of silver
Fifth Layer: Intermediate Layer
  Same as the Second Layer
Sixth Layer: First Green-Sensitive Emulsion Layer
  A silver iodobromide emulsion (iodide content: 6 mol%), silver coated amount: 1.8 g/m$^2$
    Sensitizing Dye III: $5 \times 10^{-4}$ mol per mol of silver
    Sensitizing Dye IV: $2 \times 10^{-4}$ mol per mol of silver
    Coupler EX-4: 0.05 mol per mol of silver
    Coupler EX-5: 0.008 mol per mol of silver
    Coupler EX-9: 0.0015 mol per mol of silver
Seventh Layer: Second Green-Sensitive Emulsion Layer
  A silver iodobromide emulsion (iodide content: 8 mol%), silver coated amount: 1.3 g/m$^2$
    Sensitizing Dye III: $3 \times 10^{-4}$ mol per mol of silver
    Sensitizing Dye IV: $1.2 \times 10^{-4}$ mol per mol of silver
    Coupler EX-7: 0.003 mol per mol of silver
Eighth Layer: Yellow Filter Layer
  A gelatin layer containing yellow colloidal silver and a dispersion of 2,5-di-tert-octylhydroquinone
Ninth Layer: First Blue-Sensitive Emulsion Layer
  A silver iodobromide emulsion (iodide content: 6 mol%), silver coated amount: 0.7 g/m$^2$
    Coupler EX-8: 0.25 mol per mol of silver
    Coupler EX-9: 0.015 mol per mol of silver
Tenth Layer: Second Blue-Sensitive Emulsion Layer
  A silver iodobromide emulsion (iodide content: 6 mol%), silver coated amount: 0.6 g/m$^2$
    Coupler EX-8: 0.06 mol per mol of silver
Eleventh Layer: First Protective Layer
  A gelatin layer containing silver iodobromide (iodide content: 1 mol%, average particle size: 0.07$\mu$, silver coated amount: 0.5 g/m$^2$) and a dispersion of Ultraviolet Ray Absorbing Agent UV-1).
Twelfth Layer: Second Protective Layer
  A gelatin layer containing polymethyl methacrylate particles (having a diameter of about 1.5$\mu$)

Gelatin Hardener H-1 and a surface active agent were incorporated into each of the layers in addition to the above-described components.

The sample thus-prepared was designated Sample 101.

Samples 101 to 110 were prepared in the same manner as described for Sample 101 except changing Coupler EX-9 used in the first green-sensitive emulsion layer to the compounds as shown in Table 1 below, respectively.

The structures of the compounds used for preparing these samples were as follows.

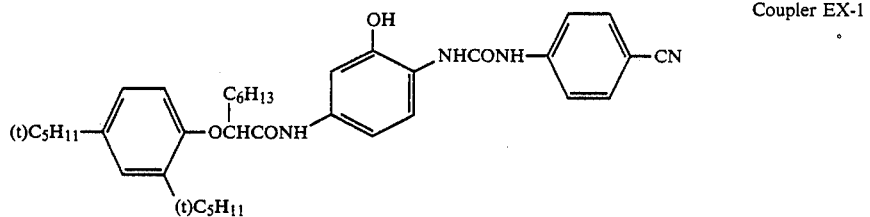
Coupler EX-1
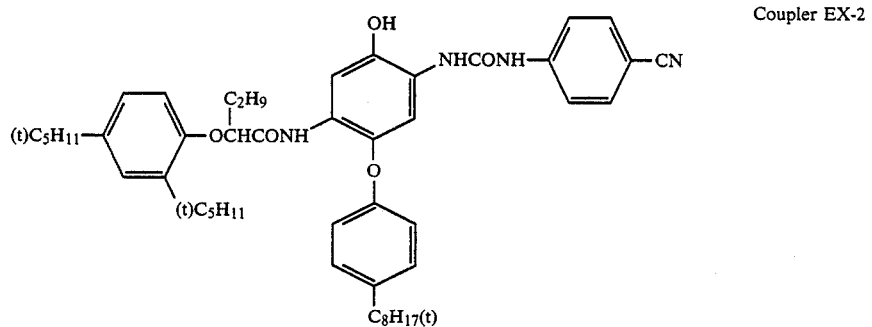
Coupler EX-2
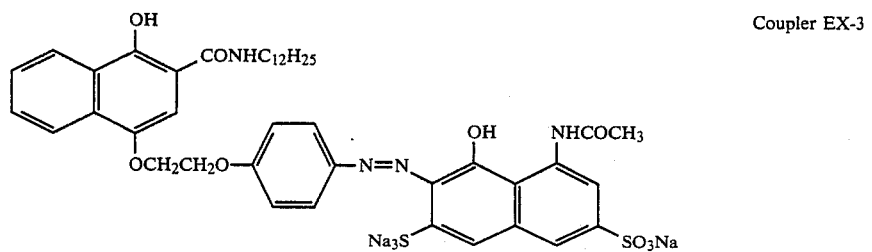
Coupler EX-3
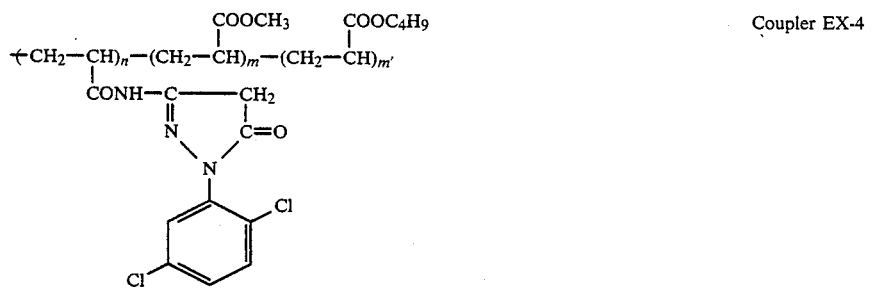
Coupler EX-4
n/m + m' = 1 (weight ratio)
m/m' = 1 (weight ratio)
molecular weight: about 40,000
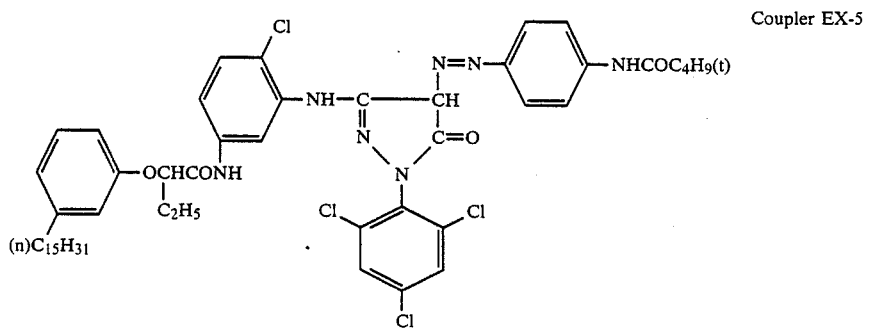
Coupler EX-5

Coupler EX-6
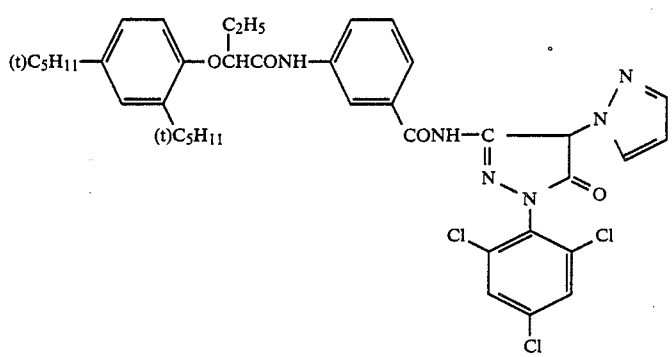
Coupler EX-7
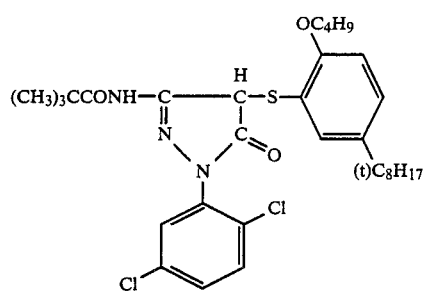
wherein (t)C$_8$H$_{17}$ represents (CH$_3$)$_3$CCH$_2$$\overset{|}{C}$(CH$_3$)$_2$
(coupler as described in U.S. Pat. No. 4,146,396)   Coupler EX-9
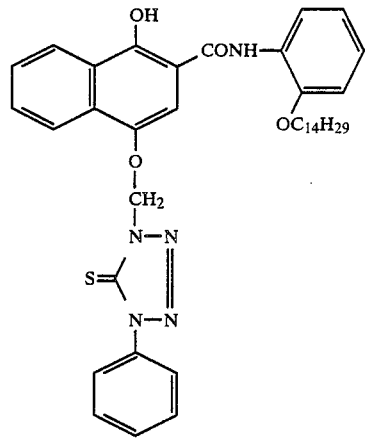
(coupler as described in U.S. Pat. No. 4,248,962)   Coupler EX-11
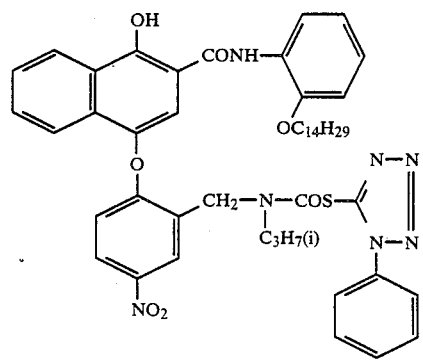
Coupler EX-8
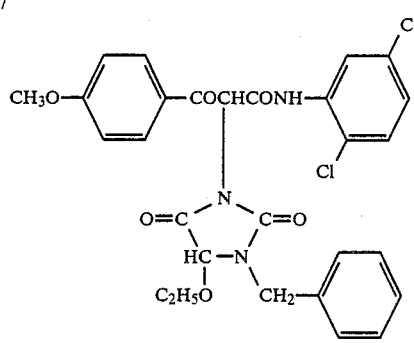
(coupler as described in U.S. Pat. No. 4,438,193)   Coupler EX-10
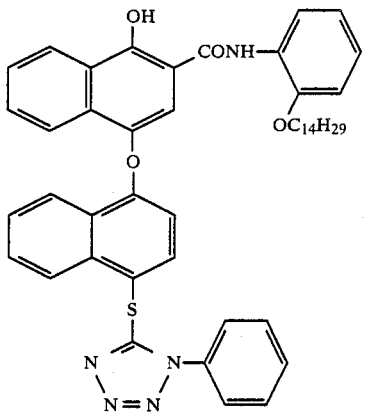
H-1
CH$_2$=CH—SO$_2$—CH$_2$CONH—CH$_2$
CH$_2$=CH—SO$_2$—CH$_2$CONH—CH$_2$

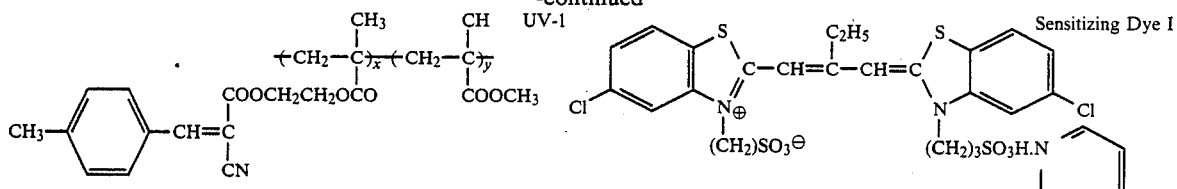

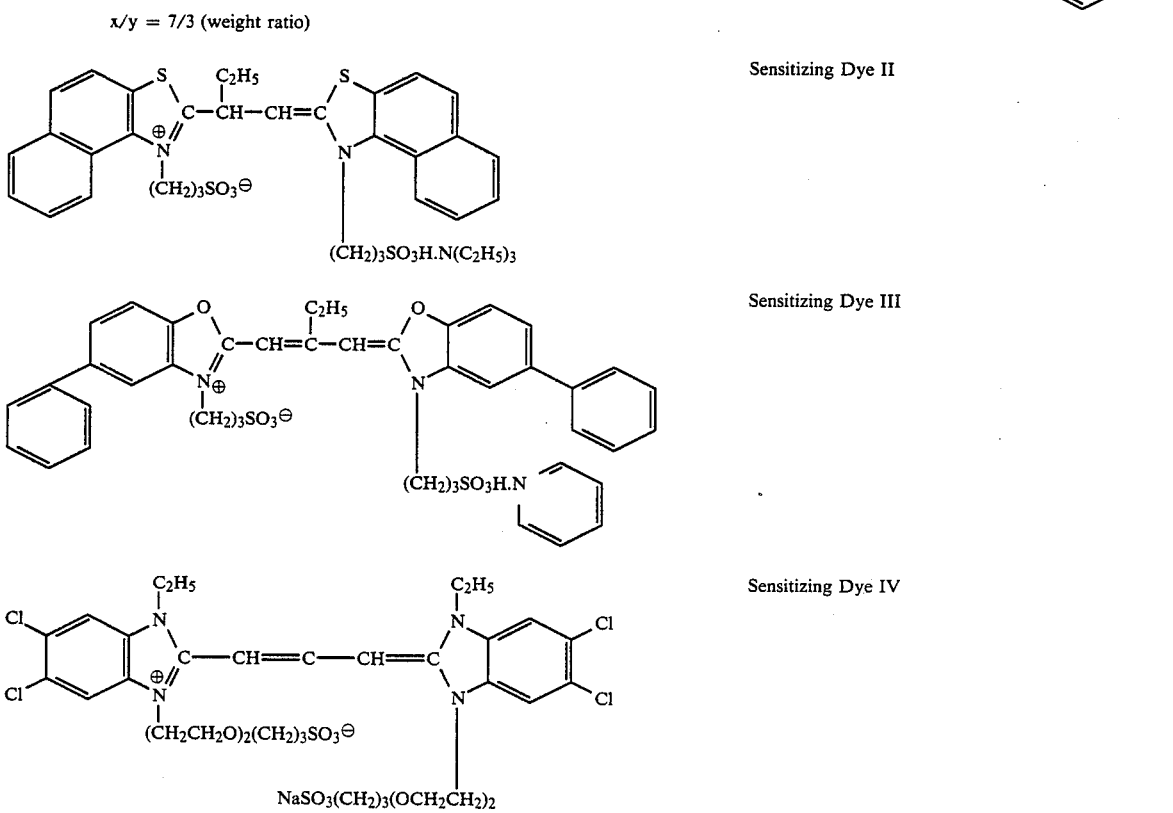

Samples 101 to 110 were subjected to wedge exposure to white light and then development processing at 38° C. according to the following processing steps.

| 1. Color development | 3 min. 15 sec. |
|---|---|
| 2. Bleaching | 6 min. 30 sec. |
| 3. Washing with water | 2 min. 10 sec. |
| 4. Fixing | 4 min. 20 sec. |
| 5. Washing with water | 3 min. 15 sec. |
| 6. Stabilizing | 1 min. 05 sec. |

The compositions of the processing solutions used for the above-described steps were as follows.

| Color Developing Solution | |
|---|---|
| Diethylenetriaminepentaacetic acid | 1.0 g |
| 1-Hydroxyethylidene-1,1-diphosphonic acid | 2.0 g |
| Sodium sulfite | 4.0 g |
| Potassium carbonate | 30.0 g |
| Potassium bromide | 1.4 g |
| Potassium iodide | 1.3 mg |
| Hydroxylamine sulfate | 2.4 g |
| 4-(N—Ethyl-N—β-hydroxyethylamino)-2-methylaniline sulfate | 4.5 g |
| Water to make | 1.0 liter |
| | (pH 10.0) |
| Bleaching Solution: | |
| Ammonium ethylenediaminetetraacetato iron (III) | 100.0 g |
| Disodium ethylenediaminetetraacetate | 10.0 g |
| Ammonium bromide | 150.0 g |
| Ammonium nitrate | 10.0 g |
| Water to make | 1.0 liter |
| | (pH 6.0) |
| Fixing Solution: | |
| Disodium ethylenediaminetetraacetate | 1.0 g |
| Sodium sulfite | 4.0 g |
| Ammonium thiosulfate (70% aqueous solution) | 175.0 ml |
| Sodium hydrogensulfite | 4.6 g |
| Water to make | 1.0 liter |
| | (pH 6.6) |
| Stabilizing Solution: | |
| Formalin (40%) | 2.0 ml |
| Polyoxyethylene p-monononylphenyl ether (average polymerization degree: about 10) | 0.3 g |
| Water to make | 1.0 liter |

The samples thus-processed exhibited almost the same sensitivity and gradation. The sharpness of the green-sensitive layers of these samples were evaluated using conventional MTF (modulation transfer function) values at spatial frequencies of 4 cycles/mm and 40 cycles/mm. The results obtained are shown in Table 1 below.

TABLE 1

| Sample | Coupler Added to* First Green-Sensitive Layer | Amount** Added | MTF Value 4 cycles/mm | MTF Value 40 cycles/mm |
|---|---|---|---|---|
| 101 (Comparison) | EX-9 | 1.0 | 1.15 | 0.45 |
| 102 (Comparison) | EX-10 | 1.5 | 1.17 | 0.46 |
| 103 (Comparison) | EX-11 | 1.0 | 1.16 | 0.45 |
| 104 (Present Invention) | (1) | 1.5 | 1.25 | 0.54 |
| 105 (Present Invention) | (2) | 1.5 | 1.26 | 0.54 |
| 106 (Present Invention) | (3) | 3.0 | 1.28 | 0.56 |
| 107 (Present Invention) | (7) | 1.5 | 1.27 | 0.54 |
| 108 (Present Invention) | (8) | 1.5 | 1.27 | 0.55 |
| 109 (Present Invention) | (19) | 2.0 | 1.28 | 0.56 |
| 110 (Present Invention) | (20) | 3.5 | 1.29 | 0.55 |

*Compound added in place of Coupler EX-9 to the first green-sensitive emulsion layer.
**Amount added is indicated using a molar ratio taking the mole of Coupler EX-9 added as 1.

From the results shown in Table 1 above, it is understood that the MTF values in the case of using the compounds according to the present invention are extremely high in comparison with the case of using conventional DIR couplers.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least one silver halide emulsion layer, said color photographic material containing a compound capable of releasing a group, upon reaction with an oxidation product of a developing agent, which is oxidized and undergoes a ring cleavage reaction whereby a photographically useful group is cleaved, wherein said compound is represented by formula (I)

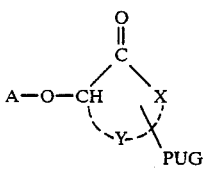

wherein A represents a coupler residue; X represents an oxygen atom, a sulfur atom or a substituted or unsubstituted imino group; Y represents an organic atomic group necessary for forming a 5-membered to 8-membered ring together with

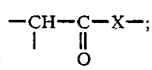

and PUG represents a photographically useful group or a precursor thereof.

2. a silver halide color photographic material as in claim 1, wherein the coupler residue represented by A is a yellow coupler residue, a magenta coupler residue, a cyan coupler residue or a non-color forming coupler residue.

3. A silver halide color photographic material as in claim 1, wherein A represents a coupler residue represented by formula (Cp-1) or (Cp-2)

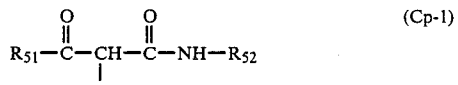

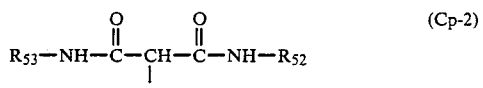

wherein $R_{51}$ represents an aliphatic group, an aromatic group, an alkoxy group or a heterocyclic group; and $R_{52}$ and $R_{53}$ each represents an aromatic group or a heterocyclic group.

4. a silver halide color photographic material as in claim 3, wherein the aliphatic group represented by $R_{51}$ is an unsubstituted alkyl group or a substituted alkyl group with a substituent selected from an alkoxy group, an aryloxy group, an amino group, an acylamino group and a halogen atom.

5. A silver halide color photographic material as in claim 3, wherein the aromatic group represented by $R_{51}$, $R_{52}$, or $R_{53}$ is an unsubstituted phenyl group or a substituted phenyl group with a substituent selected from an alkyl group, an alkenyl group, alkoxy group, an alkoxycarbonyl group, an alkoxycarbonylamino group, an aliphatic amido group, an alkylsulfamoyl group, an alkylsulfonamido group, an alkylureido group, an alkyl-substituted succinimido group, an aryloxy group, an aryloxycarbonyl group, an arylcarbamoyl group, an arylamido group, an arylsulfamoyl group, an arylsulfonamido group, an arylureido group, an amino group, a hydroxy group, a carboxy group, a sulfo group, a nitro group, a cyano group, a thiocyano group, and a halogen atom.

6. A silver halide color photographic material as in claim 3, wherein the aromatic group represented by $R_{51}$, $R_{52}$, or $R_{53}$ is a naphthyl group, a quinolyl group, an isoquinolyl group, a chromanyl group, a coumaranyl group, or a tetrahydronaphythyl group.

7. A silver halide color photographic material as in claim 3, wherein the alkoxy group represented by $R_{51}$ is an alkoxy group in which the alkyl moiety represents a straight chain or branched chain alkyl group having from 1 to 32 carbon atoms, an alkenyl group, a cyclic alkyl group or a cyclic alkenyl group, each of which may be substituted with a substituent selected from a halogen atom, an aryl group, and an alkoxy group.

8. A silver halide color photographic material as in claim 3, wherein the heterocyclic group represented by $R_{51}$, $R_{52}$, or $R_{53}$ is a group derived from a hetero ring selected from thiophene, furan, pyran, pyrrole, pyrazole, pyridine, pyrazine, pyrimidine, pyridazine, indolizine, imidazole, thiazole, oxazole, triazine, thiadiazole, and oxazine.

9. A silver halide color photographic material as in claim 1, wherein A represents a coupler residue represented by formula (Cp-3), (Cp-4), (Cp-5), and (Cp-6)

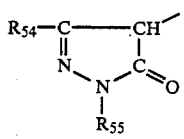

(Cp-3)

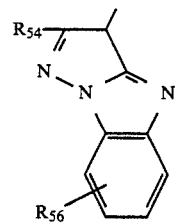

(Cp-4)

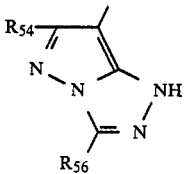

(Cp-5)

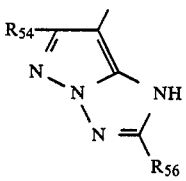

(Cp-6)

wherein $R_{55}$ represents a straight chain or branched chain alkyl group having from 1 to 32 carbon atoms, an alkenyl group, a cyclic alkyl group, an aralkyl group, or a cyclic alkenyl group, each of which may be substituted with a substituent selected from a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acrylanilino group, a hydroxy group, and a mercapto group; an aryl group, which may be substituted with a substituent selected from an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acrylanilino group, and a hydroxy group; a heterocyclic group, which may be substituted with a substituent selected from the substituents as defined for the above-described aryl group; an aliphatic acyl group; an aromatic acyl group; an alkylsulfonyl group; an arylsulfonyl group; an alkylcarbamoyl group; an arylcarbamoyl group; an alkylthiocarbamoyl group; or an arylthiocarbamoyl group; $R_{54}$ represents a hydrogen atom, a straight chain or branched chain alkyl group having from 1 to 32 carbon atoms, an alkenyl group, a cyclic alkyl group, an aralkyl group, a cyclic alkenyl group, an aryl group or a heterocyclic group each of which may be substituted with the substituents as defined for these groups of $R_{55}$, respectively; an alkoxycarbonyl group; an aryloxycarbonyl group; an aralkyloxycarbonyl group; an alkoxy group; an aryloxy group, an alkylthio group; an arylthio group; a carboxy group, an acylamino group; a diacylamino group; an N-alkylacylamino group, an N-arylacylamino group; a ureido group; a urethane group; a thiourethane group; an arylamino group; an alkylamino group; a cycloamino group; a heterocyclic amino group; an alkylcarbonyl group; an arylcarbonyl group; a sulfonamido group; a carbamoyl group; a sulfamoyl group; a cyano group; a hydroxy group; or a sulfo group; and $R_{56}$ represents a hydrogen atom; a straight chain or branched chain alkyl group having from 1 to 32 carbon atoms, an alkenyl group, a cyclic alkyl group, an aralkyl group, a cyclic alkenyl group, an aryl group or a heterocyclic group each of which may be substituted with a substituent selected from the substituents as defined for the groups of $R_{55}$, respectively; a cyano group; an alkoxy group, an aryloxy group, a halogen atom, a carboxy group, an alkoxycarbonyl group, an aryloxycarbonyl group, an acyloxy group, a sulfo group, an acyl group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, or an N-acylanilino group.

10. A silver halide color photographic material as in claim 1, wherein A represents a coupler residue represented by formula (Cp-7), (Cp-8), or (Cp-9)

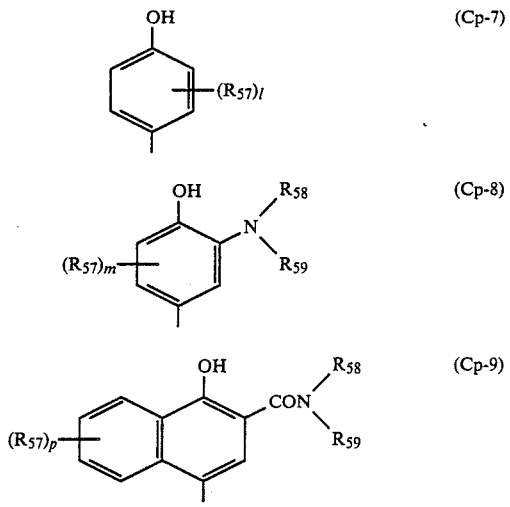

wherein $R_{57}$ represents a hydrogen atom, a halogen atom, an alkoxycarbonylamino group, an aliphatic hydrocarbon residue, an N-arylureido group, an acylamino group, or an —O—$R_{62}$ group or an —S—$R_{62}$ group wherein $R_{62}$ represents an aliphatic hydrocarbon group; $R_{58}$ and $R_{59}$ each represents hydrogen, an aliphatic hydrocarbon group, an aryl group, or a heterocyclic group, provided that no more than one of $R_{58}$ and $R_{59}$ represents a hydrogen atom, or $R_{58}$ and $R_{59}$ may combine with each other to form a nitrogen-containing heterocyclic nucleus; l represents an integer of 1 to 4; m represents an integer of 1 to 3; and p represents an integer of 1 to 5.

11. A silver halide color photographic material as in claim 10, wherein the aliphatic hydrocarbon group, the aryl group, or the heterocyclic group represented by $R_{57}$, $R_{58}$ or $R_{59}$ may be substituted with a substituent selected from a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, and a morpholino group.

12. A silver halide color photographic material as in claim 1, wherein A represents a coupler residue represented by the following general formula (Cp-10) or (Cp-11)

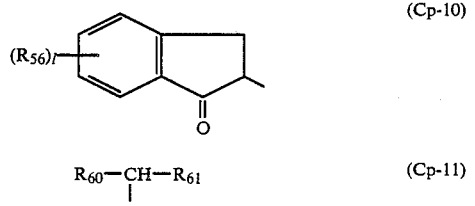

wherein $R_{60}$ represents an arylcarbonyl group, an alkanoyl group having from 2 to 32 carbon atoms, an arylcarbamoyl group, an alkanecarbamoyl group having from 2 to 32 carbon atoms, an alkoxycarbonyl group having from 1 to 32 carbon atoms or an aryloxycarbonyl group each of which may be substituted with a substituent selected from an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group, and an aryl group; and $R_{61}$ represents an arylcarbonyl group, an alkanoyl group having from 2 to 32 carbon atoms, an alkoxycarbonyl group having from 1 to 32 carbon atoms, an aryloxycarbonyl group, an alkylsulfonyl group having from 1 to 32 carbon atoms, an arylsulfonyl group, an aryl group or a 5-membered or 6-membered heterocyclic group each of which may be substituted with a substituent selected from the substituents as defined for $R_{60}$; $R_{56}$ represents a hydrogen atom; a straight chain or branched chain alkyl group having from 1 to 32 carbon atoms, an alkenyl group, a cyclic alkyl group, an aralkyl group, a cyclic alkenyl group, an aryl group, or a heterocyclic group, each of which may be substituted with a substituent selected from the substituents as defined for the groups of $R_{55}$, respectively; a cyano group; an alkoxy group, an aryloxy group, a halogen atom, a carboxy group, an alkoxycarbonyl group, an aryloxycarbonyl group, an acyloxy group, a sulfo group, an acyl group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group or an N-acylanilino group; and l represents an integer of 1 to 4.

13. A silver halide color photographic material as in claim 3, wherein A represents a coupler residue represented by formula (Cp-1) wherein $R_{51}$ represents a tert-butyl group or a substituted or unsubstituted aryl group and $R_{52}$ represents a substituted or unsubstituted aryl group.

14. A silver halide color photographic material as in claim 3, wherein A represents a coupler residue represented by formula (Cp-2) wherein $R_{52}$ and $R_{53}$ each represents a substituted or unsubstituted aryl group.

15. A silver halide color photographic material as in claim 9, wherein A represents a coupler residue represented by formula (Cp-3) wherein $R_{54}$ represents an acylamino group, a ureido group, or an arylamino group, and $R_{55}$ represents a substituted aryl group.

16. A silver halide color photographic material as in claim 9, wherein A represents a coupler residue represented by formula (Cp-4) wherein $R_{54}$ represents an acylamino group, a ureido group, or an arylamino group, and $R_{56}$ represents a hydrogen atom.

17. A silver halide color photographic material as in claim 9, wherein A represents a coupler residue represented by formula (Cp-5) or (Cp-6) wherein $R_{54}$ and $R_{56}$ each represents a straight chain or branched chain alkyl group, an alkenyl group, a cyclic alkyl group, an aralkyl group, or a cyclic alkenyl group.

18. A silver halide color photographic material as in claim 10, wherein A represents a coupler residue represented by formula (Cp-7) wherein $R_{57}$ represents an acylamino group or a ureido group at the 2-position, an acylamino group or an alkyl group at the 5-position, and a hydrogen atom or a chlorine atom at the 6-position.

19. A silver halide color photographic material as in claim 10, wherein A represents a coupler residue represented by formula (Cp-9) wherein $R_{57}$ represents a hydrogen atom, an acylamino group, a sulfonamido group, or an alkoxycarbonyl group at the 5-position, $R_{58}$ represents a hydrogen atom, and $R_{59}$ represents a phenyl group, an alkyl group, an alkenyl group, a cyclic alkyl group, an aralkyl group, or a cyclic alkenyl group.

20. A silver halide color photographic material as in claim 12, wherein A represents a coupler residue represented by formula (Cp-10) wherein $R_{56}$ represents an acylamino group, a sulfonamido group, or a sulfamoyl group.

21. A silver halide color photographic material as in claim 12, wherein A represents a coupler residue represented by formula (Cp-11) wherein $R_{60}$ and $R_{61}$ each represents an alkoxycarbonyl group.

22. A silver halide color photographic material as in claim 1, wherein the compound is a polymeric coupler containing a coupler moiety derived from a compound represented by formula (I).

23. A silver halide color photographic material as in claim 22, wherein the polymeric coupler is selected from a polymer derived from a monomeric coupler represented by formula (Cp-12) and having a recurring unit represented by formula (Cp-13) and a copolymer of at least one kind of the above-described monomeric coupler and at least one of a noncolor forming monomer having at least one ethylene group which does not have an ability of coupling with the oxidation product of an aromatic primary amine developing agent, wherein formulae (Cp-12) and (Cp-13) are represented by

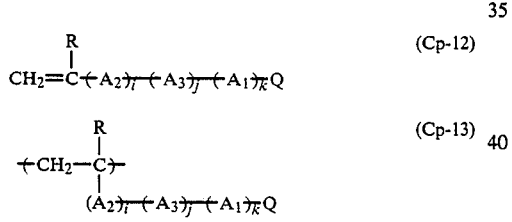

wherein R represents a hydrogen atom, a lower alkyl group having from 1 to 4 carbon atoms, or a chlorine atom; $A_1$ represents —CONR'—, —NR'CONR'—, —NR'COO—, —COO13 , —SO$_2$—, —CO—, —NR'CO—, —SO$_2$NR'—, —NR'SO$_2$—, —OCO—, —OCONR'—, —NR'— or —O—; $A_2$ represents —CONR'— or —COO—; R' represents a hydrogen atom, an aliphatic group or an aryl group, and when two or more groups are present in one molecule, they may be the same or different; $A_3$ represents a substituted or unsubstituted alkylene group having from 1 to 10 carbon atoms, a substituted or unsubstituted aralkylene group, or a substituted or unsubstituted arylene group; Q represents a coupler residue which is connected through any of the groups represented by $R_{51}$ to $R_{61}$ in the general formulae (Cp-1) to (Cp-11); and i, j, and k each represents 0 or 1.

24. A silver halide color photographic material as in claim 23, wherein the substituent for the alkylene group, aralkylene group or arylene group represented by $A_3$ is selected from an aryl group, a nitro group, a hydroxy group, a cyano group, a sulfo group, an alkoxy group, an aryloxy group, an acyloxy group, an acylamino group, a sulfonamido group, a sulfamoyl group, a halogen atom, a carboxy group, a carbamoyl group, an alkoxycarbonyl group, and a sulfonyl group.

25. A silver halide color photographic material as in claim 23, wherein the non-color forming monomer is selected from an acrylic acid, an ester, or amide derived from an acrylic acid, methylenebisacrylamide, a vinyl ester, an acylonitrile, an aromatic vinyl compound, a maleic acid derivative, and a vinylpyridine.

26. A silver halide color photographic material as in claim 1, wherein a group represented by X and Y is a group represented by formula (II), (III), (IV), (V), (VI), (VII), (VIII), or (IX)

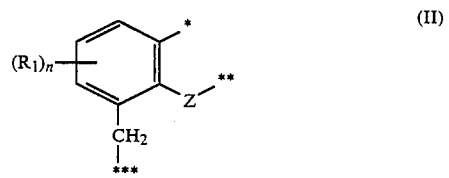

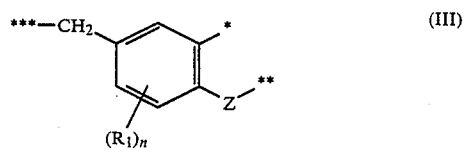

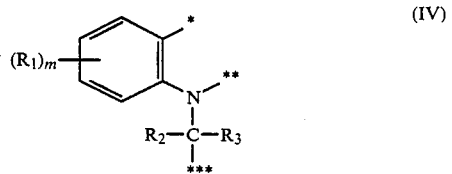

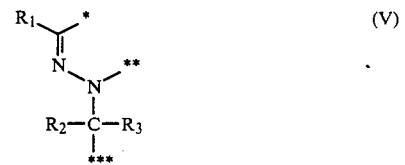

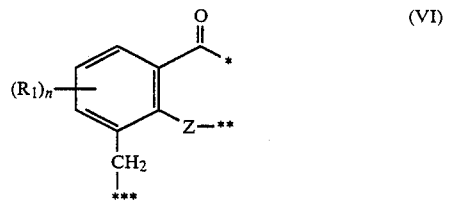

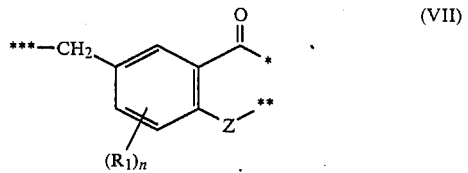

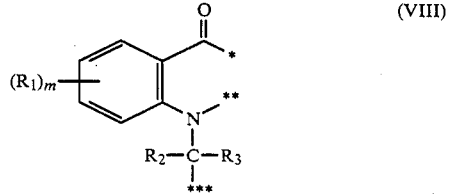

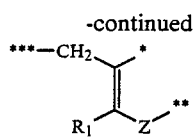

(IX)

wherein a bond indicated by * denotes the position at which the group is connected to CH of formula (I), a bond indicated by  denotes the position at which the group is connected to the carbonyl group of formula (I), and a bond indicated by * denotes the position at which the group is connected to PUG of formula (I); $R_1$ represents a hydrogen atom or a group capable of being substituted on an aromatic ring; Z represents —O—, —S—, or

wherein $R_5$ represents $R_4$, $R_4CO-$, $R_4SO_2-$ or $R_4NHCO-$, wherein $R_4$ represents an aliphatic group, an aromatic group or a heterocyclic group; n represents an integer of 1 to 3, m represents an integer of 1 to 4; and $R_2$ and $R_3$ each represents a hydrogen atom or a group capable of being substituted at a methylene group.

27. A silver halide color photographic material as in claim 26, wherein $R_1$ represents a hydrogen atom, a halogen atom, an aliphatic group, an aromatic group, a heterocyclic group, $R_4O-$, $R_4S-$, $R_4OOC-$, $R_4CO-$, $R_4CONH-$, $R_2SO_2NH-$, $R_4NHSO_2-$, $R_4NHCO-$, a hydroxy group, a nitro group, a cyano group, $R_4NHCONH-$, $R_4COO-$, or a carboxy group, etc., wherein $R_4$ represents an aliphatic group, an aromatic group, or a heterocyclic group.

28. A silver halide color photographic material as in claim 26, wherein $R_2$ and $R_3$ each represents a hydrogen atom, $R_4OOC-$, $R_4CO-$, an aromatic group, or a heterocyclic group, wherein $R_4$ represents an aliphatic group, an aromatic group, or a heterocyclic group.

29. A silver halide color photographic material as in claim 26, wherein the group represented by X and Y is a group represented by formula (IV).

30. A silver halide color photographic material as in claim 1, wherein the photographically useful group represented by PUG is a group of a development inhibitor, a development accelerator, a silver halide solvent, a dye, a fogging agent, a developing agent, a coupler, a fixing accelerator, or a fixing inhibitor.

31. A silver halide color photographic material as in claim 30, wherein the photographically useful group is a development inhibitor selected from a 5-aryltetrazolylthio group, a 5-aliphatic group substituted tetrazolylthio group, a benzimidazolylthio group, a benzothiazolylthio group, a benzoxazolylthio group, a benzotriazolyl group, a benzindazolyl group.

32. A silver halide color photographic material as in claim 1, wherein said compound is present in a silver halide emulsion layer or a layer adjacent thereto.

33. A silver halide color photographic material as in claim 32, wherein the amount of compound is in a range from $1 \times 10^{-6}$ mol to 1 mol per mol of silver halide present in the silver halide emulsion layer.

* * * * *